(12) United States Patent
Carling et al.

(10) Patent No.: US 9,522,890 B2
(45) Date of Patent: *Dec. 20, 2016

(54) COMPOUNDS ACTING AT MULTIPLE PROSTAGLANDIN RECEPTORS GIVING A GENERAL ANTI-INFLAMMATORY RESPONSE

(71) Applicant: Allergan, Inc., Irvine, CA (US)

(72) Inventors: William R. Carling, Bishops Stortford (GB); Jose L. Martos, Baslidon (GB); Jussi J. Kangasmetsa, Safron Walden (GB); Jenny W. Wang, Irvine, CA (US); David F. Woodward, Lake Forest, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/798,143

(22) Filed: Jul. 13, 2015

(65) Prior Publication Data

US 2016/0068491 A1    Mar. 10, 2016

Related U.S. Application Data

(63) Continuation of application No. 13/723,856, filed on Dec. 21, 2012, now Pat. No. 9,090,566.

(60) Provisional application No. 61/580,495, filed on Dec. 27, 2011.

(51) Int. Cl.
    *C07D 231/14* (2006.01)
(52) U.S. Cl.
    CPC .................... *C07D 231/14* (2013.01)
(58) Field of Classification Search
    None
    See application file for complete search history.

(56) References Cited

U.S. PATENT DOCUMENTS

| | | | |
|---|---|---|---|
| 4,166,452 | A | 9/1979 | Generales |
| 4,256,108 | A | 3/1981 | Theeuwes |
| 4,265,874 | A | 5/1981 | Bonsen |
| 6,511,999 | B2 | 1/2003 | Burk |
| 2004/0162323 | A1 | 8/2004 | Krauss |
| 2005/0065200 | A1 | 3/2005 | Woodward |
| 2007/0060596 | A1 | 3/2007 | Giblin |

FOREIGN PATENT DOCUMENTS

| | | |
|---|---|---|
| WO | 2005-040128 | 5/2005 |
| WO | 2006-114313 | 11/2006 |
| WO | 2012-003414 | 1/2012 |

OTHER PUBLICATIONS

Castellani, ML et al, Anti-Chemokine Therapy for Inflammatory Diseases, International Journal of Immunopathology and Pharmacology, 2007, 447-453, 20(3), US.

Conti, P. et al, MCP-1 and RANTES Are Mediators of Acute and Chronic Inflammation, Allergy and Asthma Proc, 2001, 133-137, 22, US.

Garcia, Gilles et al, New Chemokine Targets for Asthma Therapy, Current Allergy and Asthma Reports, 2005, 155-160, 5, US.

Gleissner, Christian A. et al, Platelet Chemokines in Vascular Disease, ATVB in Focus Chemokines in Atherosclerosis, Thrombosis, and Vascular Biology, 2008, 1920-1927, 28, US.

Ho, Cy et al, Suppressive effect of combination treatment of leflunomide and methotrexate on chemokine expression in patients with rheumatoid arthritis, Clin Exp Immunol, 2003, 132-138, 133, US.

Iwamoto, Takuji et al, Molecular aspects of rheumatoid arthritis: chemokines in the joints of patients, The FEBS Journal, 2008, 4448-4455, 275, US.

Matias, I., Prostaglandin Ethanolamides (Prostamides): In Vitro Pharmacology and Metabolism, The Journal of Pharmacology and Experimental Therapeutics, Jan. 29, 2004, 745-757, 209(2), US.

Pivarcsi, Andor et al, Chemokine Networks in Atopic Dermatitis: Traffic Signals of Disease, Current Allergy and Asthma Reports, 2005, 284-290, 5, US.

Qi, Xu-Feng et al, the adenylyl cyclase-cAMP system suppresses TARC/CCL17 and MDC/CCL22 production through p38 MAPK and NF-KB in HaCaT keratinocytes, Molecular Immunology, 2009, 1925-1934, 46, US.

Remingtons, Remingtons_16th, Pharmaceutical Sciences, 1980, 1-10, 16, Remingtons_16th.

Woodward, David et al, Characterization of Receptor Subtypes Involved in Prostanoid-Induced Conjunctival Pruritus and Their Role in Mediating Allergic Conjunctival Itching, The Journal of Pharmacology and Experimental Therapeutics, 1996, 137-142, 279.

Zernecke, Alma, Chemokines in Atherosclerosis an Update, Arterioscler Thromb Vasc Biol, 2008, 1897-1908, 28, US.

Hal, Adrian, et al., Novel methylene-linked heterocyclic EP1 receptor antagonists, Bioorganic & Medicinal Chemistry Letters 2008, 18:1592-1597.

Patent Cooperation Treaty, Notification of Transmittal of the International Search Report and the Written Opinion of the International Searching Authority, or the Declaration, Form PCT/ISA/220, Int. App. No. PCT/US2012/071232, May 2, 2013.

*Primary Examiner* — Kamal Saeed
(74) *Attorney, Agent, or Firm* — Jonathan Bass

(57) ABSTRACT

The present invention provides a compound, that is

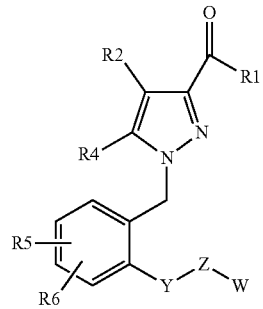

wherein Y, W, Z, R1, R2, R4, R5 and R6 are as defined in the specification.

The compounds may be administered to treat DP, FP, EP1, TP and/or EP4 receptor-mediated diseases or conditions.

4 Claims, No Drawings

COMPOUNDS ACTING AT MULTIPLE PROSTAGLANDIN RECEPTORS GIVING A GENERAL ANTI-INFLAMMATORY RESPONSE

CROSS REFERENCE TO RELATED APPLICATIONS

This application is a continuation of U.S. patent application Ser. No. 13/723,856 filed Dec. 21, 2012, which in turn claims the benefit of U.S. Provisional Patent Application No. 61/580,495, filed on Dec. 27, 2011, the disclosure of each of which is incorporated herein by reference in their entireties.

BACKGROUND OF THE INVENTION

1. Field of the Invention

This invention relates to compounds, to processes for their preparation, to pharmaceutical compositions containing them and to their use in medicine, in particular their use in the treatment of conditions mediated by the action of ligands for the $DP_1$, FP, TP, $EP_1$ and $EP_4$ prostaglandin (PG) receptors. The present compounds have the general structure shown below and act at different prostaglandin receptors to thereby provide a general anti-inflammatory response.

2. Summary of the Related Art

The $EP_1$ receptor is a 7-transmembrane receptor and its natural ligand is the prostaglandin $PGE_2$. $PGE_2$ also has affinity for the other EP receptors (types $EP_2$, $EP_3$ and $EP_4$). The $EP_1$ receptor is associated with smooth muscle contraction, pain (in particular inflammatory, neuropathic and visceral), inflammation, allergic activities, renal regulation and gastric or enteric mucus secretion.

Prostaglandin $E_2$ ($PGE_2$) exerts allodynia through the $EP_1$ receptor subtype and hyperalgesia through $EP_2$ and $EP_3$ receptors in the mouse spinal cord. Furthermore, it has been shown that in the $EP_1$ knock-out mouse pain-sensitivity responses are reduced by approximately 50%.

$EP_1$ receptor antagonist (ONO-8711) reduces hyperalgesia and allodynia in a rat model of chronic constriction injury and inhibits mechanical hyperalgesia in a rodent model of post-operative pain. The efficacy of $EP_1$ receptor antagonists in the treatment of visceral pain in a human model of hypersensitivity has been demonstrated. Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects. Moreover, as a result of sparing potentially beneficial prostaglandin pathways, these agents may have enhanced efficacy and safety over NSAIDS and/or COX-2 inhibitors. $EP_4$ receptors have also been implicated in pain, hyperalgesia, allodynia, and inflammation. (See Pub. No. US 2005/0065200 for other diseases that may be treated by EP4 receptor antagonists.)

The TP (also known as $TxA_2$) receptor is a prostanoid receptor subtype stimulated by the endogenous mediator thromboxane. Activation of this receptor results in various physiological actions primarily incurred by its platelet aggregatory and smooth muscle constricting effects, thus opposing those of prostacyclin receptor activation.

TP receptors have been identified in human kidneys in the glomerulus and extraglomerular vascular tissue. Activation of TP receptors constricts glomerular capillaries and suppresses glomerular filtration rates indicating that TP receptor antagonists could be useful for renal dysfunction in glomerulonephritis, diabetes mellitus and sepsis.

Activation of TP receptors induces bronchoconstriction, an increase in microvascular permeability, formation of mucosal edema and mucus secretion, which are typical characteristic features of bronchial asthma. TP antagonists have been investigated as potential asthma treatments resulting in, for example, orally active Seratrodast (AA-2414).

Ramatroban is another TP receptor antagonist currently undergoing phase III clinical trials as an anti-asthmatic compound.

Since $DP_1$ receptor stimulation may trigger an asthmatic response in certain individuals, compounds that have $DP_1$ antagonist properties may be useful as anti-asthmatic drugs. (See Pub. No. 2004/0162323 for the disclosure of other diseases and conditions that may be treated with DP antagonists.)

Finally, the FP receptor modulates intraocular pressure and mediates smooth muscle contraction of the sphincter muscles in the gastrointestinal tract and the uterus. Thus, antagonists of the FP receptor are useful for treating reproductive disorders. (See U.S. Pat. No. 6,511,999 for other diseases and conditions that may be treated with FP receptor antagonists.)

As further background for the present invention, see US Published Patent Application 2007/0060596.

BRIEF SUMMARY OF THE INVENTION

This invention provides novel compounds, that are 1-[(5-halo or alkyl or fluoroalkyl or alkoxy-2-{(cycloalkyl)oxy}phenyl)methyl]-(5-alkyl or fluoroalkyl)-1H-pyrazole-3-(carboxylic acid or methylene carboxylic acids) and alkyl or aryl ester or sulfonamides thereof Preferably the ester or sulfonamide is an alkyl ester or sulfonamide. Preferably said compound is a 1-[(5-halo-2-{(cycloalkyl)oxy}phenyl)methyl]-(5-alkyl)-1H-pyrazole-3-(carboxylic acid) or an alkyl or aryl ester or sulfonamide thereof. Preferably, said halo is chloro or bromo and said cycloalkylalkyl is cyclopentyl The invention further relates to pharmaceutical compositions containing the above compounds in combination with a pharmaceutically-acceptable excipient and to their use in medicine, in particular their use in the treatment of conditions mediated by the action of ligands for the $DP_1$, FP, $EP_1$ and $EP_4$ prostaglandin (PG) receptors. The compounds of this invention are also useful for treating conditions mediated by the action of ligands for the thromboxane (TP) receptor.

Some embodiments of the present invention include:

1. A compound, that is a 1-[(5-halo or alkyl or fluoroalkyl or alkoxy-2-{(cycloalkyl)oxy}phenyl)methyl]-(5-alkyl or fluoroalkyl)-1H-pyrazole-3-(carboxylic acid or methylene carboxylic acid) or an alkyl or aryl ester or sulfonamide thereof.

2. A compound according to paragraph 1 wherein said compound is a 1-({5-halo-2-[(2-cycloalkyl)oxy]phenyl}methyl)-3-carboxylic acid or ester or sulfonamide thereof.

3. A compound according to paragraph 1 wherein said compound is a 1-({5-halo-2-[(2-cycloalkyl)oxy]phenyl}methyl)-3-carboxylic acid.

4. A compound according to paragraph 2 wherein said ester or sulfonamide is an alkyl ester or sulfonamide.

5. A compound according to paragraph 3, wherein said halo is selected from the group consisting of chloro and bromo.

6. A compound represented by the following formula

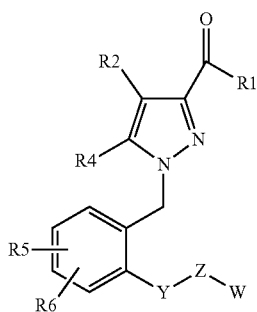

wherein Y is $(CH_2)_m$ wherein m is 0 or an integer of from 1 to 3;
Z is selected from the group consisting of O, S, SO, $SO_2$ and $(CH_2)_p$, wherein p is 0 or an integer of from 1 to 3;
W is substituted phenyl ring, alkyl, substituted alkyl, cycloalkyl or substituted cycloalkyl:
$R_1$ is selected from the group consisting of $OR_7$, $N(R_7)_2$, and $N(R_7)SO_2R_7$;
$R_2$ is H;
$R_4$ is selected from the group consisting of alkyl, halogen-substituted alkyl and amino,
$R_5$ is selected from the group consisting of H, hydroxyl, alkyl, aryl, alkoxy, aryloxy, halogen, nitro, amino, cyano and hydroxyl, halogen, nitro, amino and cyano-substituted alkyl, aryl, alkoxy or aryloxy;
$R_6$ is selected from the group consisting of H, hydroxyl, alkyl, aryl, alkoxy, aryloxy, halogen, nitro, amino, cyano and hydroxyl, halogen, nitro, amino and cyano-substituted alkyl, aryl, alkoxy or aryloxy, wherein at least one of $R_5$ and $R_6$ is halogen; and
$R_7$ is selected from the group consisting of H, hydrocarbyl and substituted hydrocarbyl.

8. The compound of paragraph 7 wherein $R_1$ is OH.

9. The compound of paragraph 8 wherein $R_7$ is selected from the group consisting of carbocyclic aryl and alkyl 10. The compound of paragraph 9 wherein W is cycloalkyl.

11. The compound of paragraph 10 wherein $R_4$ is selected from the group consisting of alkyl and chloro and bromo-substituted alkyl.

12. The compound of paragraph 10 wherein $R_4$ is H.

13. The compound of paragraph 10 wherein Y is absent, i.e. n is 0.

14. The compound of paragraph 10 wherein Z is O.

15. The compound of paragraph 10 wherein W is cyclopentyl

16. The compound of paragraph 10 that is selected from the group consisting of
1-(5-Chloro-2-cyclopentylmethoxy-benzyl)-5-methyl-1H-pyrazole-3-carboxylic acid,
1-(5-Bromo-2-cyclopentylmethoxy-benzyl)-5-methyl-1H-pyrazole-3-carboxylic acid and
1-(5-Bromo-2-cyclobutylmethoxy-benzyl)-5-methyl-1H-pyrazole-3-carboxylic acid 17. A method comprising administering a compound represented by the following formula

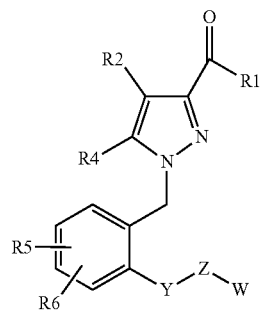

wherein Y is $(CH_2)_m$ wherein m is 0 or an integer of from 1 to 3;
Z is selected from the group consisting of O, S, SO, $SO_2$ and $(CH_2)_p$, wherein p is 0 or an integer of from 1 to 3;
W is substituted phenyl ring, alkyl, substituted alkyl, cycloalkyl or substituted cycloalkyl:
$R_1$ is selected from the group consisting of $OR_7$, $N(R_7)_2$, and $N(R_7)SO_2R_7$;
$R_2$ is H;
$R_4$ is selected from the group consisting of alkyl, halogen-substituted alkyl and amino;
$R_5$ is selected from the group consisting of H, hydroxyl, alkyl, aryl, alkoxy, aryloxy, halogen, nitro, amino, cyano and hydroxyl, halogen, nitro, amino and cyano-substituted alkyl, aryl, alkoxy or aryloxy;
$R_6$ is selected from the group consisting of H, hydroxyl, alkyl, aryl, alkoxy, aryloxy, halogen, nitro, amino, cyano and hydroxy, halogen, nitro, amino and cyano-substituted alkyl, aryl, alkoxy or aryloxy, wherein at least one of $R_5$ and $R_6$ are halogen; and
$R_7$ is selected from the group consisting of H, hydrocarbyl and substituted hydrocarbyl.

18. The method of paragraph 17 wherein $R_1$ is OH.

19. The method compound of paragraph 18 wherein $R_7$ is selected from the group consisting of carbocyclic aryl and alkyl 20. The method of paragraph 19 wherein W is cycloalkyl.

21. The method of paragraph 20 wherein $R_4$ is selected from the group consisting of alkyl and chloro and bromo-substituted alkyl.

22. The method of paragraph 20 wherein $R_4$ is H.

23. The method of paragraph 20 wherein Y is absent, i.e. n 24. The method of paragraph 20 wherein Z is O. is 0.

25. The compound of paragraph 20 wherein W is cyclopentyl

26. The compound of paragraph 20 that is selected from the group consisting of
1-(5-Chloro-2-cyclopentylmethoxy-benzyl)-5-methyl-1H-pyrazole-3-carboxylic acid,
1-(5-Bromo-2-cyclopentylmethoxy-benzyl)-5-methyl-1H-pyrazole-3-carboxylic acid and
1-(5-Bromo-2-cyclobutylmethoxy-benzyl)-5-methyl-1H-pyrazole-3-carboxylic acid 27. The method of paragraph 26 wherein said compound is administered to treat DP1, FP, EP1, TP and/or EP4 receptor mediated diseases or conditions.

28. The method of paragraph 27 wherein said condition or disease is related to inflammation.

29. The method of paragraph 27 wherein said DP1, FP, EP1, TP and/or EP4 receptor mediated condition or disease is selected from the group consisting of allergic conditions, asthma, allergic asthma, allergic rhinitis, uveitis and related disorders, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, endometriosis, fertility disorders, gangrene, glaucoma, hyperpyrexia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, pre-term labor rheumatoid arthritis, pain, perennial rhinitis, pulmonary congestion, pulmonary hypotension, Raynaud's disease, rejection in organ transplant and by-pass surgery, respiratory conditions, hirsutism, rhinorrhea, shock, sleep disorders, and sleep-wake cycle disorders.

30. The method of paragraph 27 wherein said compound is administered as a surgical adjunct in ophthalmology for cataract removal and artificial lens insertion, ocular implant procedures, photorefractive radial keratotomy and other ophthalmogical laser procedures.

31. The method of paragraph 27 wherein said compound is administered as a surgical adjunct in a procedure involving skin incisions, relief of pain and inflammation and scar formation/keloids post-surgery, for treating sports injuries and general aches and pains in muscles and joints.

32. The method of paragraph 27 wherein said $DP_1$, FP, $EP_1$, TP, and/or $EP_4$ receptor mediated condition or disease is an $EP_1$ and/or $EP_4$ receptor mediated condition or disease.

33. The method of paragraph 27 wherein said $DP_1$, FP, $EP_1$, TP and/or $EP_4$ receptor mediated condition or disease is an allergic condition.

34. The method of paragraph 33 wherein said condition is dermatological allergy.

35. The method of paragraph 27 wherein said condition is an ocular allergy.

36. The method of paragraph 27 wherein said condition is a respiratory allergy.

37. The method of paragraph 27 wherein said condition or disease is selected from the group consisting of nasal congestion, rhinitis, and asthma.

38. The method of paragraph 27 wherein said condition or disease is related to pain.

39. The method of paragraph 27 wherein said condition or disease is selected from the group consisting of arthritis, migraine, and headache.

40. The method of paragraph 27 wherein said condition or disease is associated with the gastrointestinal tract.

41. The method of paragraph 27 wherein said condition or disease is selected from the group consisting of peptic ulcer, heartburn, reflux esophagitis, erosive esophagitis, non-ulcer dyspepsia, infection by *Helicobacter pylori*, alrynitis, and irritable bowel syndrome.

42. The method of paragraph 27 wherein said condition or disease is selected from the group consisting of hyperalgesia and allodynia.

43. The method of paragraph 27 wherein said condition or disease is related to mucus secretion.

44. The method of paragraph 27 wherein said mucus secretion is gastrointestinal.

45. The method of paragraph 27 wherein said mucus secretion occurs in the nose, sinuses, throat, or lungs.

46. The method of paragraph 27 wherein said condition or disease is related to abdominal cramping.

47. The method of paragraph 27 wherein said condition or disease is irritable bowel syndrome.

48. The method of paragraph 27 wherein said condition or disease is a bleeding disorder.

49. The method of paragraph 27 wherein said condition or disease is a sleep disorder.

50. The method of paragraph 27 wherein said condition or disease is mastocytosis.

51. The method of paragraph 27 wherein said condition or disease is associated with elevated body temperature.

52. The method of paragraph 27 wherein said condition or disease is associated with ocular hypertension and glaucoma.

53. The method of paragraph 27 wherein said condition or disease is associated with ocular hypotension.

54. The method of paragraph 27 wherein said condition relates to surgical procedures to treat pain, inflammation and other unwanted sequelae wherein said surgical procedure includes incision, laser surgery or implantation.

55. The method of paragraph 27 where said condition is related to pain and inflammation and post-surgical scar and keloid formation.

56. The method of paragraph 27 where said condition is related to diseases of female reproduction, associated with menstrual cramping, endometriosis, and pre-term labor 57 A pharmaceutical product comprising a compound having the following formula

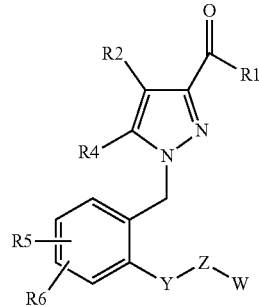

Y is $(CH_2)_m$ wherein m is 0 or an integer of from 1 to 3;
Z is selected from the group consisting of O, S, SO, $SO_2$ and $(CH_2)_p$, wherein p is 0 or an integer of from 1 to 3;
W is substituted phenyl ring, alkyl, substituted alkyl, cycloalkyl or substituted cycloalkyl:
$R_1$ is selected from the group consisting of $OR_7$, $N(R_7)_2$, and $N(R_7)SO_2R_7$;
$R_2$ is H;
$R_4$ is selected from the group consisting of alkyl, halogen-substituted alkyl and amino;
$R_5$ is selected from the group consisting of H, hydroxyl, alkyl, aryl, alkoxy, aryloxy, halogen, nitro, amino, cyano and hydroxy, halogen, nitro, amino and cyano-substituted alkyl, aryl, alkoxy or aryloxy;
$R_6$ is selected from the group consisting of H, hydroxyl, alkyl, aryl, alkoxy, aryloxy, halogen, nitro, amino, cyano and hydroxy, halogen, nitro, amino and cyano-substituted alkyl, aryl, alkoxy or aryloxy, wherein at least one of $R_5$ and $R_6$ are halogen; and
$R_7$ is selected from the group consisting of H, hydrocarbyl and substituted hydrocarbyl.
or a pharmaceutically acceptable salt or a prodrug thereof, wherein said product is packaged and labeled for the treatment or prevention of a disease or condition selected from the group consisting of uveitis, allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, endometriosis fertility disorders, hyperpyrexia, gangrene, glaucoma, hypothermia, immune and autoimmune diseases, inflammatory conditions, menstrual cramping, metastic tumor growth, migraine, mucus secretion disorders, nasal congestion, nasal inflammation, occlusive vascular diseases, ocular hypertension, ocular hypotension, osteoporosis, pain, perennial rhinitis, pre-term labor pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, sports injuries, muscle aches and pains, and surgical adjunct for minimizing pain, inflammation and scar/keloid formation.

58. A pharmaceutical composition comprising a compound having the following formula

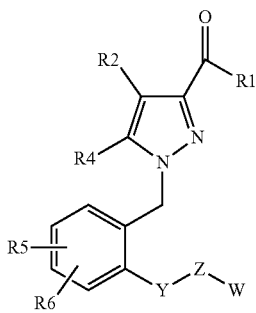

Y is $(CH_2)_m$ wherein m is 0 or an integer of from 1 to 3;
Z is selected from the group consisting of O, S, SO, $SO_2$ and $(CH_2)_p$, wherein p is 0 or an integer of from 1 to 3;
W is substituted phenyl ring, alkyl, substituted alkyl, cycloalkyl or substituted cycloalkyl;
$R_1$ is selected from the group consisting of $OR_7$, $N(R_7)_2$, and $N(R_7)SO_2R_7$;
$R_2$ is H;
$R_4$ is selected from the group consisting of alkyl, halogen-substituted alkyl and amino;
$R_5$ is selected from the group consisting of H, hydroxyl, alkyl, aryl, alkoxy, aryloxy, halogen, nitro, amino, cyano and hydroxy, halogen, nitro, amino and cyano-substituted alkyl, aryl, alkoxy or aryloxy;
$R_6$ is selected from the group consisting of H, hydroxyl, alkyl, aryl, alkoxy, aryloxy, halogen, nitro, amino, cyano and hydroxy, halogen, nitro, amino and cyano-substituted alkyl, aryl, alkoxy or aryloxy, wherein at least one of $R_5$ and $R_6$ are halogen; and

DETAILED DESCRIPTION OF THE INVENTION

The following terms are used to define the disclosed invention.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc."

"Alkyl" refers to a straight-chain, branched or cyclic saturated aliphatic hydrocarbon. Preferably, the alkyl group has 1 to 12 carbons. More preferably, it is an alkyl of from 4 to 10 carbons, most preferably 4 to 8 carbons. Typical alkyl groups include methyl, ethyl, propyl, isopropyl, butyl, isobutyl, tertiary butyl, pentyl, hexyl and the like. The alkyl group may be optionally substituted with one or more substituents selected from the group consisting of hydroxyl, cyano, alkoxy, =O, =S, $NO_2$, halogen, dimethyl amino, and SH.

"Cycloalkyl" refers to a cyclic saturated aliphatic hydrocarbon group. Preferably, the cycloalkyl group has 3 to 12 carbons. More preferably, it has from 4 to 7 carbons, most preferably 5 or 6 carbons.

"Substituted cycloalkyl" refers to a cycloalkyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc. Specific\substituted cycloalkyls, i.e. cyclopentyl, may be referred to as substituted cyclopentyl with the understanding that the substituents are the same."

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of alkyl, hydroxyl, halogen, $COOR^6$, $NO_2$, $CF_3$, $N(R^6)_2$, $CON(R^6)_2$, $SR^6$, sulfoxy, sulfone, CN and $OR^6$, wherein $R^6$ is alkyl.

"Carbocyclic aryl" refers to an aryl group wherein the ring atoms are carbon.

"Heteroaryl or heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like. Preferably, the heteroaryl group has from 2 to 10 carbons. More preferably, it has from 3 to 10 carbons, most preferably 3 carbons.

The present invention provides compounds having the general formula I:

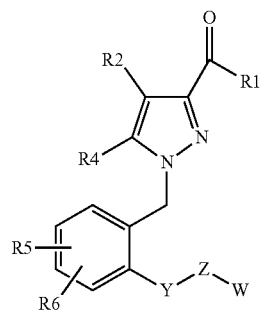

Y is $(CH_2)_m$ wherein m is 0 or an integer of from 1 to 3;
Z is selected from the group consisting of O, S, SO, $SO_2$ and $(CH_2)_p$, wherein p is 0 or an integer of from 1 to 3;
W is substituted phenyl ring, alkyl, substituted alkyl, cycloalkyl or substituted cycloalkyl:
$R_1$ is selected from the group consisting of $OR_7$, $N(R_7)_2$, and $N(R_7)SO_2R_7$;
$R_2$ is H;
$R_4$ is selected from the group consisting of alkyl, halogen-substituted alkyl and amino;
$R_5$ is selected from the group consisting of H, hydroxyl, alkyl, aryl, alkoxy, aryloxy, halogen, nitro, amino, cyano and hydroxyl, halogen, nitro, amino and cyano-substituted alkyl, aryl, alkoxy or aryloxy;
$R_6$ is selected from the group consisting of H, hydroxyl, alkyl, aryl, alkoxy, aryloxy, halogen, nitro, amino, cyano and hydroxyl, halogen, nitro, amino and cyano-substituted alkyl, aryl, alkoxy or aryloxy, wherein at least one of $R_5$ and $R_6$ are halogen; and Preferably, $R_1$ is OH.
Preferably, Y is absent, i.e. n is 0.
Preferably, Z is O.
Preferably, W is selected from the group consisting of cyclopentyl, cyclobutyl, cyclohexyl and substituted cyclopentyl, cyclobutyl and cyclohexyl.
More preferably W is cyclopentyl and cyclobutyl.
The most preferred compounds of the present invention are selected from the group consisting of
The compounds of the present invention may be prepared by the methods disclosed in the Examples.
The following examples are intended to illustrate the present invention.
The reagents and conditions used in the Examples may be abbreviated as follows:
Ac is acetyl;
DCM is dichloromethane;
DTAD is Di-tert-butyl azodicarboxylate;
TFA is trifluoroacetic acid;
RT is room temperature;
Ph is phenyl;
DiBAL-H is diisobutylaluminumhydride;
DMF is dimethylformamide;
Et is ethyl; THF is tetrahydrofuran;
DMAP is 4-dimethylaminopyridine;
HEPES is 4-(2-hydroxyethyl)-1-piperazineethanesulfonic acid).

Example 1

1-(5-CHLORO-2-CYCLOPENTYLMETHOXY-BENZYL)-5-METHYL-1H-PYRAZOLE-3-CARBOXYLIC ACID, 4

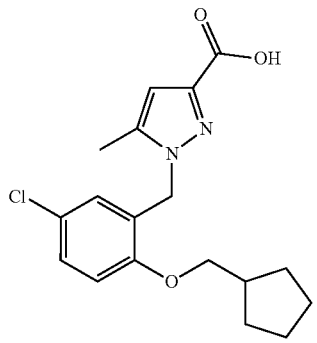 [SMILES: Cc1cc(C(=O)O)nn1Cc1cc(Cl)ccc1OCC1CCCC1]

Step 1

N'-(5-chloro-2-hydroxy-benzyl)-hydrazinecarboxylic acid tert-butyl ester, 1

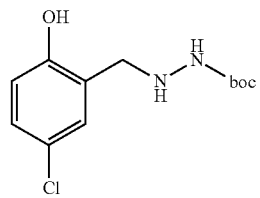

A solution of 5-chloro-2-hydroxybenzaldehyde (1.5 g 9.3 mmol), tert-butylcarbazate (1.25 g, 9.3 mmol) and acetic acid (0.54 mL, 9.3 mmol) in $CH_2Cl_2$ (50 mL) was stirred under a nitrogen atmosphere for 30 min at RT. Then sodium triacetoxyborohydride (6.20 g, 27.9 mmol) was added portion wise and the resulting mixture was stirred at RT overnight. The reaction was thoroughly quenched with 2 M HCl (15 mL) and stirred at RT for 1 h. The reaction mixture was partitioned between water (50 mL) and $CH_2Cl_2$ (25 mL). The aqueous layer was extracted with $CH_2Cl_2$ (25 mL). The combined organic layers were washed with water (2×75 mL), dried ($Na_2SO_4$) and evaporated to dryness to give hydrazine 1 as a white solid.
$^1$H-NMR (CDCl$_3$, 300 MHz) δ7.17 (dd, 1H, ArH,), 7.03 (d, 1H, ArH), 6.83 (d, 1H, ArH), 1.49 (s, 9H, —C(CH$_3$)$_3$).
LC-MS: m/z 273 M+H$^+$

Step 2

1-(5-chloro-2-hydroxy-benzyl)-5-methyl-1 h-pyrazole-3-carboxylic acid ethyl ester, 2

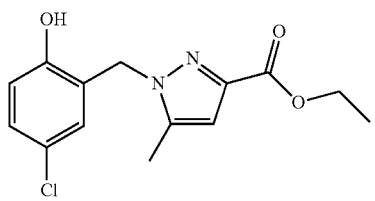

A suspension of N'-(5-chloro-2-hydroxy-benzyl)-hydrazinecarboxylic acid tert-butyl ester 1 (2.5 g, 9.3 mmol) in $CH_2Cl_2$ was treated with TFA (20 mL) and stirred at RT overnight. The volatiles were removed in vacuo. The residue was dissolved in AcOH (20 mL) and slowly added to a solution of ethyl-2,4-dioxopentanoate in AcOH (10 mL). The resulting mixture was refluxed for 1 h and let cool down and stirred at RT for 16 h. Precipitated 1-(5-Chloro-2-hydroxy-benzyl)-5-methyl-1H-pyrazole-3-carboxylic acid ethyl ester 2 was filtered and washed with ether. The white solid was dried overnight in a dessicator yielding 1-(5-chloro-2-hydroxy-benzyl)-5-methyl-1H-pyrazole-3-carboxylic acid ethyl ester 2.
$^1$H-NMR (CDCl$_3$, 300 MHz) δ10.16 (s, 1H, ArOH), 7.17 (dd, 1H, ArH), 6.86 (d, 1H, ArH), 6.65 (d, 1H, ArH), 6.58 (s, 1H, ArH), 5.24 (s, 2H, ArCH$_2$), 4.24 (q, 2H, —CH$_2$CH$_3$) 2.28 (s, 3H, CH$_3$) 1.26 (t, 3H, —CH$_2$CH$_3$). LC-MS: m/z 295 M+H$^+$

Step 3

1-(5-chloro-2-cyclopentylmethoxy-benzyl)-5-methyl-1h-pyrazole-3-carboxylic acid ethyl ester, 3

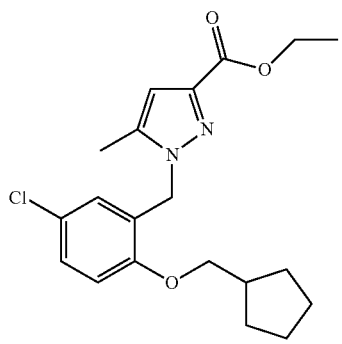 [SMILES: CCOC(=O)c1cc(C)n(Cc2cc(Cl)ccc2OCC2CCCC2)n1]

A solution of 1-(5-chloro-2-hydroxy-benzyl)-5-methyl-1H-pyrazole-3-carboxylic acid ethyl ester, 2, (0.15 g, 0.51 mmol), polymer supported triphenylphosphine (0.2 g, 0.56 mmol), diethylazodicarboxylate (0.1 g, 0.56 mmol) and cyclopentanemethanol (0.056 ml, 0.56 mmol) in a mixture of THF (5 mL) was refluxed for 48 hours. Solid support reagent was removed by filtration and the volatiles were removed in vacuo. The crude product was purified on silica to yield 1-(5-chloro-2-hydroxy-benzyl)-5-methyl-1H-pyrazole-3-carboxylic acid ethyl ester, 3a pale yellow oil, 0.0.086 g.

$^1$H-NMR (CDCl$_3$, 300 MHz) δ 7.18 (dd, 1H, ArH), 6.79 (d, 1H, ArH), 6.67 (s, 1H, ArH), 6.53 (dd, 1H, ArH), 5.37 (s, 2H, ArCH$_2$), 4.43 (q, 2H, —CH$_2$CH$_3$), 3.88 (dd, 2H, O—CH$_2$), 2.40 (m. 1H OCH$_2$CH), 2.22 (s, 3H, CH$_3$), 1.94-1.22 (m, 8H, CH$_2$), 1.42 (t, 3H, —CH$_2$CH$_3$).

LC-MS: m/z 377 M+H$^+$

Step 4

1-(5-chloro-2-cyclopentylmethoxy-benzyl)-5-methyl-1 h-pyrazole-3-carboxylic acid, 4

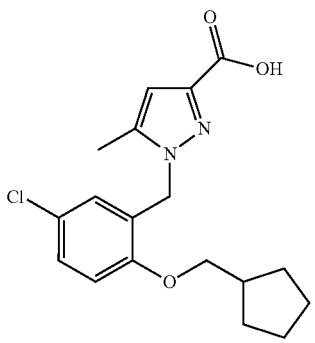

To a solution of ester 3 (0.086 g, 0.25 mmol) in MeOH (10 mL) was added a solution of 2 M NaOH 2 mL (0.40 mmol) and the resulting mixture was stirred at RT for 4 hours. The volatiles were removed in vacuo. The residue was diluted with water (5 mL) and acidified to pH 1 with 2 M HCl. The acid 4 was isolated by filtration as a white solid and washed with water and dried overnight over KOH in a dessicator to yield 1-(5-chloro-2-cyclopentylmethoxy-benzyl)-5-methyl-1H-pyrazole-3-carboxylic acid, 4, as a white solid.

$^1$H-NMR (CDCl$_3$, 300 MHz) δ 7.20 (dd, 1H, ArH), 6.81 (d, 1H, ArH), 6.71 (s, 1H, ArH), 6.63 (dd, 1H, ArH), 5.36 (s, 2H, ArCH$_2$), 3.88 (dd, 2H, O—CH$_2$), 2.40 (m. 1H OCH$_2$CH), 2.26 (s, 3H, CH$_3$), 1.94-1.22 (m, 8H, CH$_2$).

LC-MS: m/z 349 M+H$^+$

Example 2

1-(5-BROMO-2-CYCLOPENTYLMETHOXY-BENZYL)-5-METHYL-1H-PYRAZOLE-3-CARBOXYLIC ACID, 8

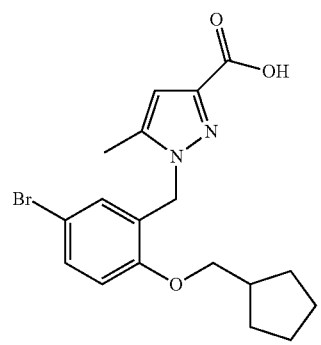 [SMILES: Cc1cc(C(=O)O)nn1Cc1cc(Cl)ccc1OCC1CCCC1]

Step 1

N'-(5-bromo-2-hydroxy-benzyl)-hydrazinecarboxylic acid tert-butyl ester, 5

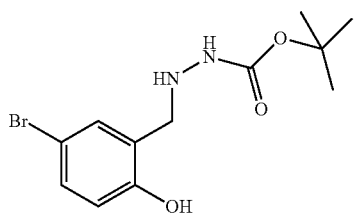 [SMILES: CC(C)(C)OC(=O)NNCc1cc(Br)ccc1O]

The title compound was prepared from 5-bromosalicaldehyde following the method in Example 1, Step 1.

$^1$H-NMR (CDCl$_3$, 300 MHz) δ7.31 (dd, 1H, ArH,), 7.17 (d, 1H, ArH), 6.79 (d, 1H, ArH), 1.49 (s, 9H, —C(CH$_3$)$_3$).

LC-MS: m/z 318 M+H$^+$

Step 2

1-(5-bromo-2-hydroxy-benzyl)-5-methyl-1 h-pyrazole-3-carboxylic acid ethyl ester, 6

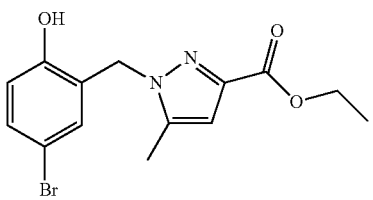 [SMILES: CCOC(=O)c1cc(C)n(Cc2cc(Br)ccc2O)n1]

The title compound was prepared from compound 5 following the method in Example 1, Step 2.

¹H-NMR (CDCl₃, 300 MHz) δ 9.51 (s, 1H, ArOH), 7.33 (dd, 1H, ArH), 7.22 (d, 1H, ArH), 6.87 (d, 1H, ArH), 6.59 (s, 1H, ArH), 5.20 (s, 2H, ArCH₂), 4.38 (q, 2H, —CH₂CH₃) 2.42 (s, 3H, CH₃) 1.40 (t, 3H, —CH₂CH₃). LC-MS: m/z 340 M+H⁺

Step 3

1-(5-bromo-2-cyclopentylmethoxy-benzyl)-5-methyl-1 h-pyrazole-3-carboxylic acid ethyl ester, 7

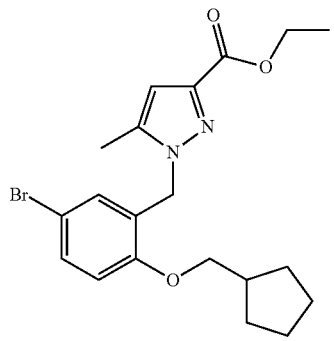 [SMILES: CCOC(=O)c1cc(C)n(Cc2cc(Br)ccc2OCC2CCCC2)n1]

The title compound was prepared from compound 6 following the method in Example 1, Step 3.

¹H-NMR (CDCl₃, 300 MHz) δ 7.24 (dd, 1H, ArH), 6.66 (d, 1H, ArH), 6.61 (dd, 1H, ArH), 6.57 (s, 1H, ArH), 5.23 (s, 2H, ArCH₂), 4.34 (q, 2H, —CH₂CH₃), 3.79 (dd, 2H, O—CH₂), 2.31 (m, 1H, OCH₂CH,) 2.13 (s, 3H, CH₂), 1.83-1.11 (m, 8H, CH₂), 1.33 (t, 3H, CH₂CH₂).

LC-MS: m/z 422 M+H⁺

Step 4

1-(5-bromo-2-cyclopentylmethoxy-benzyl)-5-methyl-1 h-pyrazole-3-carboxylic acid, 8

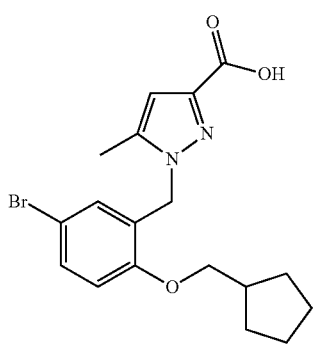

The title compound was prepared from compound 7 following the method in Example 1, Step 4.

¹H-NMR (CDCl₃, 300 MHz) δ 7.35 (dd, 1H, ArH), 6.80 (d, 1H, ArH), 6.77 (dd 1H, ArH), 6.70 (s, 1H, ArH), 5.36 (s, 2H, ArCH₂), 3.88 (dd, 2H, O—CH₂), 2.40 (m. 1H OCH₂CH), 2.27 (s, 3H, CHd, 1.94-1.10 (m, 8H, CH₂).

LC-MS: m/z 394 M+H⁺

Example 3

1-(2-CYCLOPENTYLMETHOXY-5-TRIFLUO-ROMETHYL-BENZYL)-5-METHYL-1H-PYRA-ZOLE-3-CARBOXYLIC ACID, 12

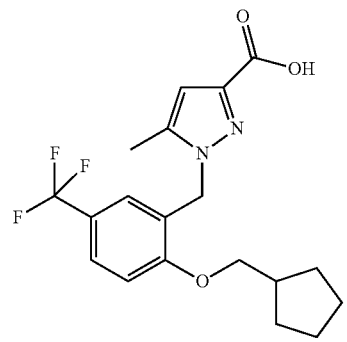 [SMILES: Cc1cc(C(=O)O)nn1Cc1cc(C(F)(F)F)ccc1OCC1CCCC1]

Step 1

N'-(2-hydroxy-5-trifluoromethyl-benzyl)-hydrazinecarboxylic acid tert-butyl ester, 9

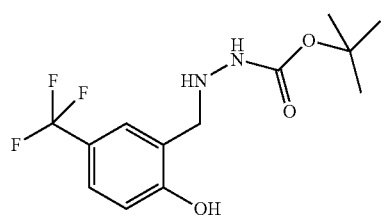 [SMILES: CC(C)(C)OC(=O)NNCc1cc(C(F)(F)F)ccc1O]

The title compound was prepared from 5-trifluoromethylalisaldehyde following the method in Example 1, Step 1.

¹H-NMR (CDCl₃, 300 MHz) δ9.71 (broad s, 1H, OH), 7.49 (dd, 1H, ArH), 7.32 (s, 1H, ArH), 6.97 (d, 1H, ArH), 6.15 (●●broad s, 1H, NH), 4.43 (●●broad s, 1H, NH), 1.50 (s, 9H, —C(CH₃)₃).

LC-MS: m/z 307 M+H⁺

Step 2

1-(2-hydroxy-5-trifluoromethyl-benzyl)-5-methyl-1 h-pyrazole-3-carboxylic acid ethyl ester, 10

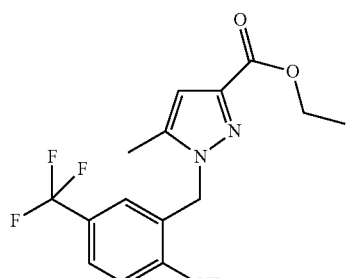

The title compound was prepared from compound 9 following the method in Example 1, Step 2.

¹H-NMR (CDCl₃, 300 MHz) δ 7.52 (dd, 1H, ArH), 7.40 (d, 1H, ArH), 7.08 (d, 1H, ArH), 6.60 (s, 1H, ArH), 5.27 (s, 2H, ArCH₂), 4.39 (q, 2H, —CH₂CH₃) 2.44 (s, 3H, CH₃) 1.40 (t, 3H, —CH₂CH₃). LC-MS: m/z 329 M+H⁺

Step 3

1-(2-cyclopentylmethoxy-5-trifluoromethyl-benzyl)-5-methyl-1 h-pyrazole-3-carboxylic acid ethyl ester, 11

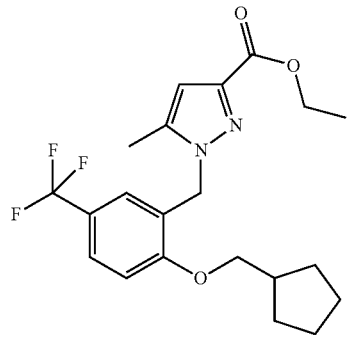 [SMILES: CCOC(=O)c1cc(C)n(Cc2cc(C(F)(F)F)ccc2OCC2CCCC2)n1]

The title compound was prepared from compound 10 following the method in Example 1, Step 3.

¹H-NMR (CDCl₃, 300 MHz) δ 7.51 (dd, 1H, ArH), 6.94 (dd, 1H, ArH), 6.85 (d, 1H, ArH), 6.67 (s, 1H, ArH), 5.42 (s, 2H, ArCH₂), 4.43 (q, 2H, —CH₂CH₃), 3.96 (dd, 2H, O—CH₂), 2.43 (m, 1H, OCH₂CH), 2.23 (s, 3H, CH₂), 1.97-1.05 (m, 8H, CH₂), 1.42 (t, 3H, CH₂CH₃).

LC-MS: m/z 411 M+H⁺

Step 4

1-(2-cyclopentylmethoxy-5-trifluoromethyl-benzyl)-5-methyl-1 h-pyrazole-3-carboxylic acid, 12

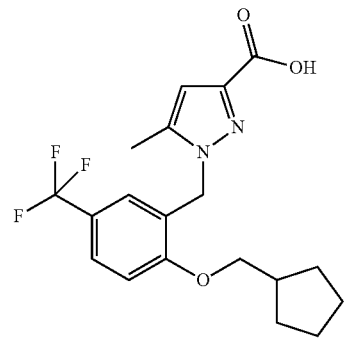 [SMILES: Cc1cc(C(=O)O)nn1Cc1cc(C(F)(F)F)ccc1OCC1CCCC1]

The title compound was prepared from compound 11 following the method in Example 1, Step 4.

¹H-NMR (CDCl₃, 300 MHz) δ 7.53 (dd, 1H, ArH), 6.96 (dd, 1H, ArH), 6.94 (d 1H, ArH), 6.72 (s, 1H, ArH), 5.40 (s, 2H, ArCH₂), 3.96 (dd, 2H, O—CH₂), 2.43 (m. 1H OCH₂CH), 2.27 (s, 3H, CHO, 1.94-1.21 (m, 8H, CH₂).

LC-MS: m/z 383 M+H⁺

Example 4

N-{1-[5-CHLORO-2-(4-METHOXY-BENZYLOXY)-BENZYL]-5-METHYL-1H-PYRAZOLE-3-CARBONYL}-BENZENESULFONAMIDE, 16

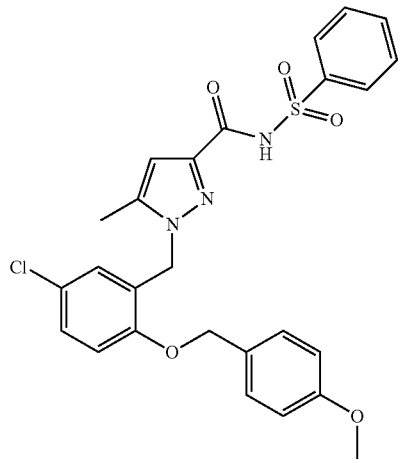 [SMILES: COc1ccc(COc2ccc(Cl)cc2Cn2nc(C(=O)NS(=O)(=O)c3ccccc3)cc2C)cc1]

Step 1

1-[5-chloro-2-(4-methoxy-benzyloxy)-benzyl]-5-methyl-1 h-pyrazole-3-carboxylic acid ethyl ester, 13

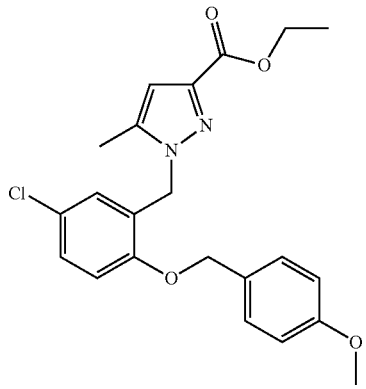 [SMILES: CCOC(=O)c1cc(C)n(Cc2cc(Cl)ccc2OCc2ccc(OC)cc2)n1]

To a solution of 1-(5-chloro-2-hydroxy-benzyl)-5-methyl-1H-pyrazole-3-carboxylic acid ethyl ester 2 0.2 g (0.6 mmol) in DMF (5 mL) were added potassium carbonate (0.23 g, 1.7 mmol), potassium iodide (0.1 g, 0.6 mmol) and 4-methoxybenzyl chloride (0.1 ml, 0.7 mmol). The resulting mixture was heated at 100° C. in an Emrys microwave reactor for 30 minutes. The volatiles were removed in vacuo. The crude product was purified on silica to yield 1-[5-chloro-2-(4-methoxy-benzyloxy)-benzyl]-5-methyl-1H-pyrazole-3-carboxylic acid ethyl ester 13 as a white solid.

¹H-NMR (CDCl₃, 300 MHz) δ 7.32 (d, 2H, ArH), 7.20 (dd, 1H, ArH,), 6.94 (d, 2H, ArH), 6.88 (d, 1H, ArH), 6.64 (s, 1H, ArH), 6.60 (d, 1H, ArH), 5.35 (s, 2H, ArCH₂), 5.03 (s, 2H, ArCH₂), 4.42 (q, 2H, —CH₂CH₃), 3.85 (3H, OCH₃), 2.15 (s, 3H, CH₃) 1.41 (t, 3H, —CH₂CH₃). LC-MS: m/z 415 M+H⁺

Step 2

1-[5-chloro-2-(4-methoxy-benzyloxy)-benzyl]-5-methyl-1h-pyrazole-3-carboxylic acid, 14

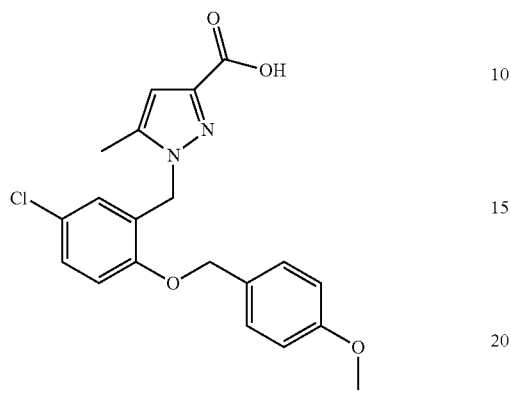

To a solution of 1-[5-chloro-2-(4-methoxy-benzyloxy)-benzyl]-5-methyl-1H-pyrazole-3-carboxylic acid ethyl ester, 13, 0.28 g (0.6 mmol) in EtOH (2 mL) was added a solution of LiOH (0.15 g in 0.5 ml H$_2$O). The resulting mixture was heated at 100° C. on microwave for 10 minutes. The mixture was poured into water (20 mL) and extracted with EtOAc (3×15 mL). The organic layers were combined, washed with brine (30 mL), dried (MgSO$_4$) and the volatiles removed in vacuo to yield 5-chloro-2-(4-methoxy-benzyloxy)-benzyl]-5-methyl-1H-pyrazole-3-carboxylic acid, 14 as a white solid.

$^1$H-NMR (CDCl$_3$, 300 MHz) δ 7.32 (d, 2H, ArH), 7.20 (dd, 1H, ArH,), 6.94 (d, 2H, ArH), 6.88 (d, 1H, ArH), 6.62 (s, 1H, ArH), 6.60 (d, 1H, ArH), 5.35 (s, 2H, ArCH$_2$), 5.03 (s, 2H, ArCH$_2$), 3.85 (3H, OCH$_3$), 2.16 (s, 3H, CH$_3$). LC-MS: m/z 387 M+H$^+$

Step 3

1-[5-chloro-2-(4-methoxy-benzyloxy)-benzyl]-5-methyl-1h-pyrazole-3-carbonyl fluoride, 15

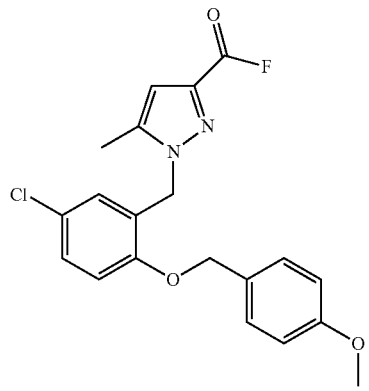 [SMILES: COc1ccc(COc2ccc(Cl)cc2Cn2nc(C(=O)F)cc2C)cc1]

To a solution of acid 5-chloro-2-(4-methoxy-benzyloxy)-benzyl]-5-methyl-1H-pyrazole-3-carboxylic acid, 14, 0.2 g (0.52 mmol) in dry THF under N$_2$ atm was added 500 μL of pyridine (6.2 mmol) and 440 μL (5.2 mmol) of cyanuric fluoride. The mixture was refluxed for 2 hours, cooled to room temperature, diluted with EtOAc and wash with water and brine. After drying over MgSO$_4$ solvents were removed in vacuo to yield the crude acid fluoride, 15 which was used in sequential step without further purification.

$^1$H-NMR (CDCl$_3$, 300 MHz) δ 7.31 (d, 2H, ArH), 7.24 (dd, 1H, ArH,), 6.94 (d, 2H, ArH), 6.91 (d, 1H, ArH), 6.76 (d, 1H, ArH), 6.70 (s, 1H, ArH), 5.35 (s, 2H, ArCH$_2$), 5.02 (s, 2H, ArCH$_2$), 3.85 (3H, OCH$_3$), 2.17 (s, 3H, CH$_3$).

$^{19}$F-NMR (CDCl$_3$, 300 MHz) δ +21.8.

Step 4 n-{1-[5-chloro-2-(4-methoxy-benzyloxy)-benzyl]-5-methyl-1h-pyrazole-3-carbonyl}-benzenesulfonamide, 16

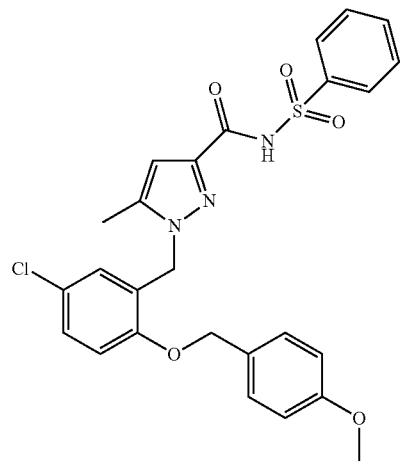 [SMILES: COc1ccc(COc2ccc(Cl)cc2Cn2nc(C(=O)NS(=O)(=O)c3ccccc3)cc2C)cc1]

To a solution of 1-[5-chloro-2-(4-methoxy-benzyloxy)-benzyl]-5-methyl-1H-pyrazole-3-carbonyl fluoride, 15, 0.06 g (0.18 mmol) and K$_2$CO$_3$ 0.100 g (0.72 mmol) in dry DCM (2 mL), benzenesulfonamide 0.055 g (0.35 mmol) was added. The mixture was stirred under a nitrogen atmosphere for 16 hours before diluting with EtOAc. The organic phase was washed with 2M HCl, followed by brine, dried over MgSO$_4$ and evaporated to dryness. The crude acyl sulphonamide was purified on silica to yield N-{1-[5-chloro-2-(4-methoxy-benzyloxy)-benzyl]-5-methyl-1H-pyrazole-3-carbonyl}-benzenesulfonamide, 16.

$^1$H-NMR (CDCl$_3$, 300 MHz) δ 8.17 (dd, 2H, ArH,), 7.96 (dd, 2H, ArH,), 7.70-7.49 (m, 3H, ArH), 7.27 (m, 2H, ArH,), 6.92 (m, 2H, ArH), 6.73 (d, 1H, ArH), 6.54 (s, 1H, ArH), 5.19 (s, 2H, ArCH$_2$), 5.00 (s, 2H, ArCH$_2$), 4.81 (broad s, 1H, NH), 3.85 (3H, OCH$_2$), 2.10 (s, 3H, CH$_3$).

LC-MS: m/z 527 M+H$^+$

Example 5

N-{1-[5-CHLORO-2-(4-CHLORO-BENZYLOXY)-BENZYL]-5-METHYL-1H-PYRAZOLE-3-CARBONYL}-BENZENESULFONAMIDE, 17

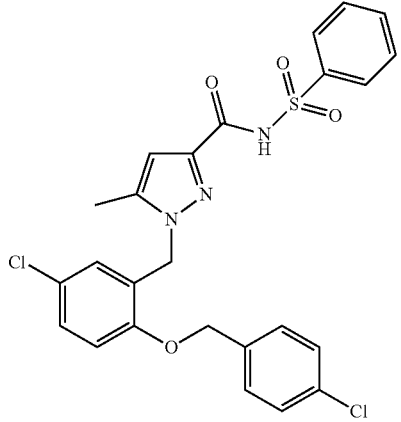 [SMILES: Cc1cc(C(=O)NS(=O)(=O)c2ccccc2)nn1Cc1cc(Cl)ccc1OCc1ccc(Cl)cc1]

The title compound was prepared following the method described in example 4 but using the appropriate reagents.

$^1$H-NMR (DMSO, 300 MHz) δ 8.17 (dd, 2H, ArH), 7.96 (dd, 2H, ArH), 7.70-7.49 (m, 3H, ArH), 7.27 (m, 2H, ArH,), 6.92 (m, 2H, ArH), 6.73 (d, 1H, ArH), 6.54 (s, 1H, ArH), 5.22 (s, 2H, ArCH$_2$), 5.19 (s, 2H, ArCH$_2$), 2.08 (s, 3H, CH$_3$).

LC-MS: m/z 530 M+H$^+$

Example 6

1-[5-BROMO-2-(2-ETHYL-BUTOXY)-BENZYL]-5-METHYL-1H-PYRAZOLE-3-CARBOXYLIC ACID, 19

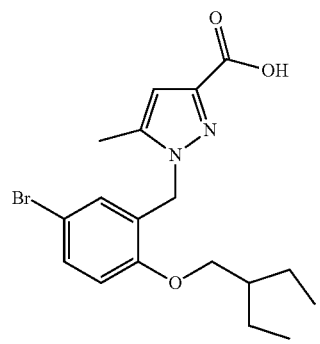 [SMILES: CCC(CC)COc1ccc(Br)cc1Cn1nc(C(=O)O)cc1C]

Step 1

1-[5-bromo-2-(-2-ethyl-butoxy)-benzyl]-5-methyl-1h-pyrazole-3-carboxylic acid ethyl ester, 18

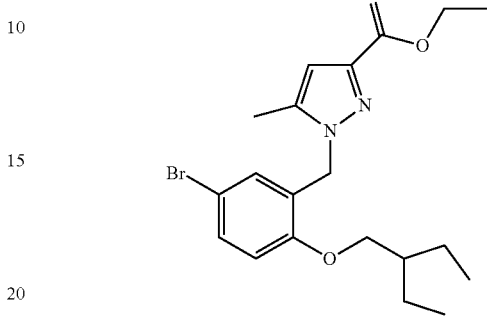

The title compound was prepared from compound 6 following the method in Example 1, Step 3.

$^1$H-NMR (CDCl$_3$, 300 MHz) δ 7.34 (dd, 1H, ArH), 6.77 (d, 1H, ArH), 6.67 (d, 1H, ArH), 6.64 (d, 1H, ArH), 5.38 (s, 2H, ArCH$_2$), 4.43 (q, 2H, —CH$_2$CH$_3$), 3.91 (dd, 2H, O—CH$_2$), 2.21 (s, 3H, CH$_2$), 1.72 (m, 1H, CH$_2$CH), 1.58-1.43 (m, 4H, CH$_2$), 1.42 (t, 3H, CH$_2$CH$_3$), 0.96 (t, 6H, CH$_2$CH$_2$).

LC-MS: m/z 424 M+H$^+$

Step 2

1-[5-bromo-2-(2-ethyl-butoxy)-benzyl]-5-methyl-1h-pyrazole-3-carboxylic acid, 19

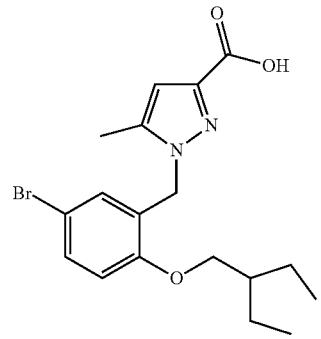 [SMILES: CCC(CC)COc1ccc(Br)cc1Cn1nc(C(=O)O)cc1C]

The title compound was prepared from compound 18 following the method in Example 4, Step 2.

$^1$H-NMR (CDCl$_3$, 300 MHz) δ 7.36 (dd, 1H, ArH), 6.78 (dd, 1H, ArH), 6.74 (d, 1H, ArH), 6.71 (d, 1H, ArH), 5.53 (s, 2H, ArCH$_2$), 3.91 (dd, 2H, O—CH$_2$), 2.25 (s, 3H, CHO, 1.72 (m, 1H, CH$_2$CH), 1.57-1.42 (m, 4H, CH$_2$), 0.96 (t, 6H, CH$_2$CH$_3$).

LC-MS: m/z 396 M+H$^+$

Example 7

1-[5-BROMO-2-(2-ETHYL-2-METHYL-BUTOXY)-BENZYL]-5-METHYL-1H-PYRAZOLE-3-CARBOXYLIC ACID, 23

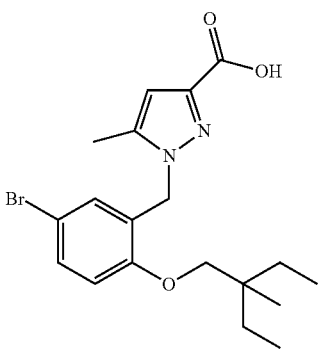 [SMILES: CCC(C)(CC)COc1ccc(Br)cc1Cn1nc(C(=O)O)cc1C]

Step 1

2-ethyl-2-methyl-butyric acid ethyl ester, 20

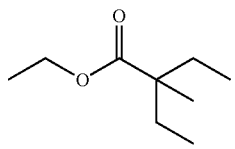

Diisopropylamine (1.13 mL, 8.05 mmol) was dissolved in THF (1 ml) under nitrogen. The mixture was cooled to −78° C. and n-Buli (3.08 mL, 7.7 mmol) was added dropwise to form LDA. A solution of 2-ethyl-butyric acid ethyl ester (0.57 mL, 3.5 mmol) in THF (2 ml) was added dropwise to this solution. The resulting mixture was stirred at −78° C. under nitrogen for 30 minutes before iodomethane (0.5 mL, 8.05 mmol) was added dropwise and the mixture was first stirred for 1 hour at −78° C., and then 30 minutes at 0° C., and finally 30 minutes at room temperature. The reaction mixture was quenched with $H_2O$ (5 ml). The mixture was extracted twice with $Et_2O$ (5 ml), washed with 2M HCl (5 ml) then dried over $MgSO_4$.

$^1$H-NMR (CDCl$_3$, 300 MHz) δ 4.14 (q, 2H, CH$_2$CH$_3$), 1.78-1.60 (m, 2H, CH$_2$CH$_3$), 1.54-1.36 (m, 2H, CH$_2$CH$_3$), 1.27 (t, 3H, CH$_2$CH$_3$), 1.11 (s, 3H, CCH$_3$), 0.84 (t, 6H, CH$_3$CH$_3$).

LC-MS: m/z 159 M+H$^+$

Step 2

2-ethyl-2-methyl-butan-1-ol, 21

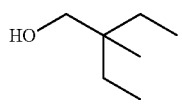

To a solution of 2-ethyl-2-methyl-butyric acid ethyl ester 20 (0.23 mL, 1.26 mmol) in dry toluene (5 ml) under nitrogen was added DIBAL-H (12.6 mL, 14.5 mmol) dropwise. The resulting mixture was stirred at room temperature for 3.5 hours. Aqueous Rochelle salts solution (10%, 15 ml) was added to the reaction mixture at 0° C. After 10 minutes at 0° C. it was stirred at room temperature for 40 minutes. The mixture was diluted with EtOAc (15 ml) and washed with 2M HCl (15 ml), saturated ammonium chloride (15 ml) and brine (15 ml) then dried over MgSO$_4$. The volatiles were removed in vacuo to yield 2-ethyl-2-methyl-butan-1-ol 21, which was used in the next step without further purification.

$^1$H-NMR (CDCl$_3$, 300 MHz) δ 3.38 (broad s, 2H, CH$_2$OH), 1.39-1.22 (m, 4H, CH$_2$CH$_3$), 1.18 (broad s, CH$_2$OH), 0.87 (s, 3H, CCH$_3$), 0.83 (t, 6H, CH$_2$CH$_3$).

LC-MS: m/z 117 M+H$^+$

Step 3

1-[5-bromo-2-(2-ethyl-2-methyl-butoxy)-benzyl]-5-methyl-1h-pyrazole-3-carboxylic acid ethyl ester, 22

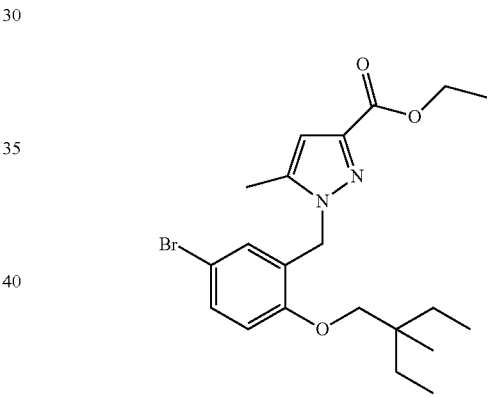

A solution of 1-(5-bromo-2-hydroxy-benzyl)-5-methyl-1H-pyrazole-3-carboxylic acid ethyl ester, 6 (0.20 g, 0.60 mmol), triphenylphosphine (0.31 g, 1.2 mmol), ditert-butylazodicarboxylate (0.27 g, 1.2 mmol) and 2-ethyl-2-methyl-butan-1-ol 20 (0.13 g, 1.2 mmol) in a mixture of THF (8 mL) was heated at 100° C. in an Emrys microwave reactor for 20 minutes. The volatiles were removed in vacuo and the crude product was purified on silica to yield 1-[5-bromo-2-(2-ethyl-2-methyl-butoxy)-benzyl]-5-methyl-1H-pyrazole-3-carboxylic acid ethyl ester, 22.

$^1$H-NMR (CDCl$_3$, 300 MHz) δ 7.32 (dd, 1H, ArH), 6.77 (d, 1H, ArH), 6.67 (s, 1H, ArH), 6.57 (d, 1H, ArH), 5.39 (s, 2H, ArCH$_2$), 4.42 (q, 2H, —CH$_2$CH$_3$), 3.68 (s, 2H, OCH$_2$), 2.20 (s, 3H, CH$_3$), 1.50-1.37 (m, 4H, CCH$_2$), 1.42 (s, 3H, CCH$_3$), 0.86 (t, 6H, CH$_2$CH$_3$).

LC-MS: m/z 438 M+H$^+$

Step 4

1-[5-bromo-2-(2-ethyl-2-methyl-butoxy)-benzyl]-5-methyl-1h-pyrazole-3-carboxylic acid, 23

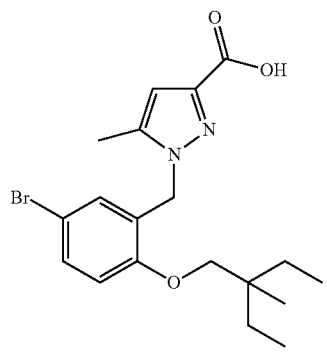 [SMILES: CCC(C)(CC)COc1ccc(Br)cc1Cn1nc(C(=O)O)cc1C]

To a solution of 1-[5-bromo-2-(2-ethyl-2-methyl-butoxy)-benzyl]-5-methyl-1H-pyrazole-3-carboxylic acid ethyl ester, 22, (0.17 g, 0.38 mmol) in a mixture of MeOH (3 mL) and THF (6 ml) was added a solution of LiOH in 3 ml of H$_2$O. The resulting mixture was heated at 100° C. in an Emrys microwave reactor for 20 minutes. The mixture was poured into water (20 mL) and extracted with EtOAc (3×15 mL). The organic layers were combined, washed with brine (30 mL), dried (MgSO$_4$) and the volatiles were removed in vacuo to yield 1-[5-bromo-2-(2-ethyl-2-methyl-butoxy)-benzyl]-5-methyl-1H-pyrazole-3-carboxylic acid, 23.

$^1$H-NMR (CDCl$_3$, 300 MHz) δ 7.34 (dd, 1H, ArH), 6.78 (d, 1H, ArH), 6.73 (s, 1H, ArH), 6.65 (d, 1H, ArH), 5.41 (s, 2H, ArCH$_2$), 3.69 (s, 2H, OCH$_2$), 2.22 (s, 3H, CH$_3$), 1.45 (q, 4H, CCH$_2$), 0.97 (s, 3H, CCH$_3$), 0.86 (t, 6H, CH$_2$CH$_3$).

LC-MS: m/z 410 M+H$^+$

Example 8

1-(5-BROMO-2-CYCLOBUTYLMETHOXY-BENZYL)-5-METHYL-1H-PYRAZOLE-3-CARBOXYLIC ACID, 25

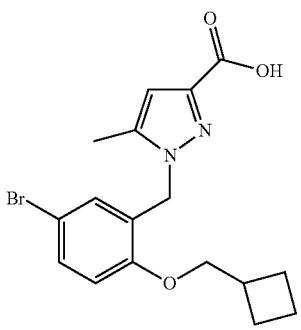

Step 1

1-(5-bromo-2-cyclobutylmethoxy-benzyl)-5-methyl-1h-pyrazole-3-carboxylic acid ethyl ester, 24

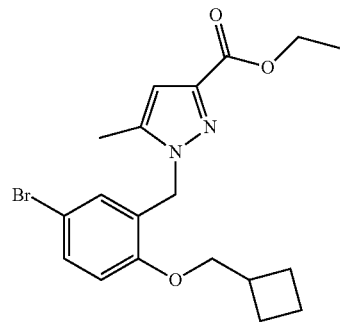 [SMILES: CCOC(=O)c1cc(C)n(Cc2cc(Br)ccc2OCC2CCC2)n1]

A solution of 1-(5-bromo-2-hydroxy-benzyl)-5-methyl-1H-pyrazole-3-carboxylic acid ethyl ester, 6 (0.1 g, 0.3 mmol), triphenylphosphine (0.155 g, 0.6 mmol), ditert-butylazodicarboxylate (0.14 g, 0.6 mmol) and cyclobutanemethanol (0.06 ml, 0.6 mmol) in a mixture of THF (8 mL) was heated at 100° C. in an Emrys microwave reactor for 20 minutes. The volatiles were removed in vacuo and the crude product was purified on silica to yield 1-[5-bromo-2-(2-ethyl-2-methyl-butoxy)-benzyl]-5-methyl-1H-pyrazole-3-carboxylic acid ethyl ester, 24.

$^1$H-NMR (CDCl$_3$, 300 MHz) δ 7.32 (m, 1H, ArH), 6.70 (d, 2H, ArH), 6.67 (s, 1H, ArH), 5.39 (s, 2H, ArCH$_2$), 4.42 (q, 2H, —CH$_2$CH$_3$), 4.00 (s, 2H, OCH$_2$), 2.80 (m, 1H, CH), 2.20 (s, 3H, CH$_2$), 2.10-1.80 (m, 6H, CCH$_2$) 1.40 (t, 3H, OCH$_2$CH$_3$).

Step 2

1-(5-bromo-2-cyclobutylmethoxy-benzyl)-5-methyl-1h-pyrazole-3-carboxylic acid, 25

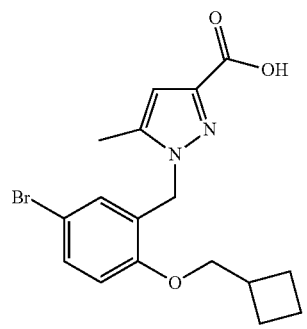 [SMILES: Cc1cc(C(=O)O)nn1Cc1cc(Br)ccc1OCC1CCC1]

To a solution of -(5-bromo-2-cyclobutylmethoxy-benzyl)-5-methyl-1h-pyrazole-3-carboxylic acid ethyl ester, 24 (0.12 g, 0.29 mmol) in a mixture of MeOH (2 mL) and THF (4 ml) was added a solution of NaOH (0.061 g, 1.45 mmol) in 2 ml of H$_2$O. The resulting mixture was heated at 100° C. in an Emrys microwave reactor for 20 minutes. The mixture was poured into water (20 mL) and extracted with EtOAc (3×15 mL). The organic layers were combined, washed with brine (30 mL), dried (MgSO$_4$) and the volatiles were removed in vacuum to yield 1-(5-bromo-2-cyclobutyl-methoxy-benzyl)-5-methyl-1 h-pyrazole-3-carboxylic acid, 25 $^1$H-NMR (CDCl$_3$, 300 MHz) δ 7.32 (d, 1H, ArH), 6.70 (m, 2H, ArH), 6.67 (s, 1H, ArH), 5.32 (s, 2H, ArCH$_2$), 3.97 (d, 2H, OCH$_2$), 2.75 (m, 1H, CH), 2.20 (s, 3H, CH$_3$), 2.10-1.80 (m, 6H, CCH$_2$)

LC-MS: m/z 380 M+H$^+$

Example 9

1-[5-BROMO-2-(1-TRIFLUOROMETHYL-CY-CLOBUTYLMETHOXY)-BENZYL]-5-METHYL-1H-PYRAZOLE-3-CARBOXYLIC ACID, 26

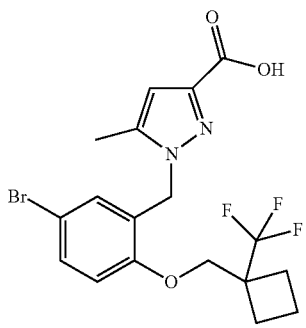 [SMILES: Cc1cc(C(=O)O)nn1Cc1cc(Br)ccc1OCC1(C(F)(F)F)CCC1]

The title compound was prepared following the methods described in example 8 but using the appropriate reagents.

$^1$H-NMR (CDCl$_3$, 300 MHz) δ 7.39 (m, 1H, ArH), 6.80 (s, 1H, ArH), 6.70 (m, 2H, ArH), 5.39 (s, 2H, ArCH$_2$), 4.19 (s, 2H, OCH$_2$), 2.45 (m, 2H, —CH$_2$CH$_2$—), 2.20 (s, 3H, CH$_3$), 2.15 (m, 4H, CCH$_2$)

LC-MS: m/z 448 M+H$^+$

The above compounds were tested for PG antagonist activity as follows using human recombinant prostanoid receptor (DP$_1$, EP$_{1-4}$, FP, IP and TP) stable cell lines:

In order to measure the response of G$_s$ and G$_i$ coupled prostanoid receptors as a Ca$^{2+}$ signal, chimeric G protein cDNAs were used. Stable cell lines over-expressing human prostanoid DP$_1$, EP$_{1-4}$, FP, IP, and TP receptors were established as follows:

Briefly, human prostanoid DP$_1$, EP$_2$, and EP$_4$ receptor cDNAs were co-transfected with chimeric G$_{qs}$ cDNA containing a haemagglutanin (HA) epitope; human prostanoid EP$_3$ receptors were co-transfected with chimeric G$_{qi}$-HA; human EP$_1$, FP, IP, and TP receptor cDNAs were expressed with no exogenous G-proteins. G$_{qs}$ and G$_{qi}$ chimeric cDNAs (Molecular Devices, Sunnyvale, Calif., U.S.A.), as well as cDNAs of prostanoid receptors, were cloned into a pCEP$_4$ vector with a hygromycin B selection marker. Transfection into HEK-293 EBNA (Epstein-Barr virus nuclear antigen) cells was achieved by the FuGENE 6 transfection Reagent (Roche Applied Science, Indianapolis, Ind., USA). Stable transfectants were selected according to hygromycin resistance. Because G$_{qs}$ and G$_{qi}$ contained an HA epitope, G-protein expression was detected by Western blotting analysis using anti-mouse HA monoclonal antibody and horseradish peroxidase (HRP)-conjugated secondary antibody, while functional expression of prostanoid receptors was detected by FLIPR screening (Matias et al., 2004). These stable cell lines were validated using previously published antagonists at 10 μM against serial dilutions of standard agonists by FLIPR functional assays for Ca$^{2+}$ Signaling (as described below).

Ca$^{2+}$ signaling studies were performed using a FLIPR TETRA system (Molecular Devices, Sunnyvale, Calif., USA) in the 384-format. This is a high-throughput instrument for cell-based assays to monitor Ca$^{2+}$ signaling associated with GPCRs and ion channels. Cells were seeded at a density of 5×10$^4$ cells/well in BioCoat poly-D-lysine coated, black wall, clear bottom 384-well plates (BD Biosciences, Franklin lakes, NJ, USA) and allowed to attach overnight in an incubator at 37° C. The cells were then washed twice with HBSS-HEPES buffer (Hanks' balanced salt solution without bicarbonate and phenol red, 20 mM HEPES, pH 7.4) using an ELx405 Select CW Microplate Washer (BioTek, Winooski, Vt., USA). After 60 min of dye-loading in the dark using the Ca$^{2+}$-sensitive dye Fluo-4AM (Invitrogen, Carlsbad, Calif., USA), at a final concentration of 2×10$^{-6}$M, the plates were washed 4 times with HBSS-HEPES buffer to remove excess dye and leaving 50 μl of buffer in each well. The plates were then placed in the FLIPR TETRA instrument and allowed to equilibrate at 37° C. Compounds were added in a 25 μl volume to each well to give final concentrations of 0.1 μM, 0.3 μM, 1 μM, 3 μM, 10 μM, and 30 μM; or 0.067 μM, 0.1 μM, 0.2 μM, 0.3 μM, 0.67 μM, and 1 μM for cells over-expressing TP receptors. After 4.5 minutes, a 7-point serial dilution of the standard agonist for the corresponding receptor, in a 25 μl volume was injected at the final concentrations from 10$^{-11}$M to 10$^{-5}$M in 10-fold serial dilution increments for cells expressing human recombinant DP$_1$, EP$_1$, EP$_2$, EP$_3$, EP$_4$, FP, and IP receptors. The dose range for the standard agonist for human recombinant TP receptors was from 10$^{-12}$M to 10$^{-6}$M. HBSS-HEPES buffer was used as the negative control for the standard agonists. Cells were excited with LED (light emitting diode) excitation at 470-495 nm and emission was measured through an emission filter at 515-575 nm. Assay plates were read for 3.5 minutes using the FLIPR$^{TETRA}$. The peak increase in fluorescence intensity was recorded for each well. On each plate, negative controls, dose response of positive controls, and co-treatments of antagonist-agonist for each dose were in triplicates. Standard agonists were as follows: DP=BW 245C, EP$_1$-EP$_4$=PGE$_2$, FP=17-phenyl-PGF$_{2α}$, IP=Cicaprost, and TP=U-46619. The peak fluorescence change in each well containing drug was expressed relative to vehicle controls with the standard agonist at 10$^{-6}$M (the positive control). To obtain concentration-response curves, compounds were tested in triplicate in each plate over the desired concentration range.

Data Processing

All plates were subjected to appropriate baseline corrections. Maximum fluorescence values were exported. The raw data of n=1 was first processed by Activity Base using nonlinear regression curve fit to calculate the percentage activity of each data point relative to the positive control (=10$^{-6}$M of the standard agonist). Then n=3 of this data were exported to GraphPad Prism 4 to calculate the average EC$_{50}$ of the standard agonist, and the IC$_{50}$ (the concentration of the antagonist required to inhibit half the standard agonist activity) were calculated using nonlinear regression curve fit, with constraints of bottom constant equal to 0 and top constant equal to 100. Calculation of Kb=[Antagonist Concentration]/(IC$_{50}$/EC$_{50}$−1). When no antagonism was detected or when Kb≥10,000 nM, the antagonist is defined as not active (NA).

The results of the above testing are reported in TABLE 1, below.

| Compound No. | FP | DP | EP1 | EP2 | EP3 | EP4 | IP | TP |
|---|---|---|---|---|---|---|---|---|
| Example 1 | 150 | 800 | 30 | NA | NA | 800 | NA | <1 |
| Example 2 | 20 | 400 | 10 | NA | NA | 400 | 1300 | <1 |
| Example 3 | 80 | 700 | 5 | 8900 | NA | 700 | 4000 | 1 |
| Example 4 | 400 | 800 | 10 | 4900 | 2500 | 140 | 900 | 2 |
| Example 5 | 1700 | 2600 | 10 | NA | 1500 | 75 | 2000 | 10 |
| Example 6 | 35 | 150 | 10 | 6200 | NA | 800 | 500 | <1 |
| Example 7 | 80 | 150 | 19 | 3600 | NA | 2070 | 1700 | 11 |
| Example 8 | 8 | 130 | 10 | NA | 4100 | 700 | 5600 | 8 |
| Example 9 | 30 | 190 | 16 | 3300 | 2600 | 600 | NA | 10 |

As shown in TABLE 1, the preferred compounds of this invention are pan antagonists which have activity at the FP, $DP_1$, $EP_1$, $EP_4$ and TP receptors, but are generally inactive at the IP, $EP_2$ and $EP_3$ receptors. Thus, these compounds have a biological selectivity profile making them useful in treating diseases and conditions which are ameliorated by the IP/$EP_2$ and/or $EP_3$ receptor stimulation, without the symptoms side effects mediated by the FP, DP, $EP_1$, $EP_4$ and TP receptors. Also, based on the data generated for this TABLE 1, it appears that the cyclobutyl and cyclopentyl compounds are more active at the FP receptor then the corresponding phenyl compounds. Therefore, cycloalkyl compounds are preferred over carbocyclic aryl compounds. Further evidence for the preference of the cycloalkyl compounds of this invention over the corresponding carbocyclic aryl compounds is that the cycloalkyl compounds are essentially inactive at $EP_2$ and $EP_3$ receptors. Thus, these compounds have a biological selectivity profile making them useful in treating diseases and conditions which are ameliorated by the IP/$EP_2$ and/or $EP_3$ receptor stimulation, without the side effects mediated by the FP, DP, $EP_1$, $EP_4$ and TP receptors.

Thus, the compounds of this invention compound may be administered to treat DP1, FP, $EP_1$, TP and/or EP4 receptor mediated diseases or conditions.

For example, said condition or disease may be related to inflammation, or said, FP, $EP_1$, TP and/or $EP_4$ receptor mediated condition or disease may be selected from the group consisting of allergic conditions, asthma, allergic asthma, allergic rhinitis, uveitis and related disorders, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, endometriosis, fertility disorders, gangrene, glaucoma, hyperpyrexia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, rheumatoid arthritis, pain, perennial rhinitis, pre-term labor, pulmonary congestion, pulmonary hypotension, Raynaud's disease, rejection in organ transplant and by-pass surgery, respiratory conditions, hirsutism, rhinorrhea, shock, sleep disorders, and sleep-wake cycle disorders.

Said compound may be administered as a surgical adjunct in ophthalmology for cataract removal and artificial lens insertion, ocular implant procedures, photorefractive radial keratotomy and other ophthalmogical laser procedures or as a surgical adjunct in a procedure involving skin incisions, relief of pain and inflammation and scar formation/keloids post-surgery, for treating sports injuries and general aches and pains in muscles and joints.

Preferably, said $DP_1$, FP, $EP_1$, TP, and/or $EP_4$ receptor mediated condition or disease is an $EP_1$ and/or $EP_4$ receptor mediated condition or disease.

Preferably, said $DP_1$, FP, $EP_1$, TP and/or $EP_4$ receptor mediated condition or disease is an allergic condition, e.g. an dermatological allergy, or an ocular allergy, or a respiratory allergy, e.g. nasal congestion, rhinitis, and asthma.

Said condition or disease may be related to pain.

Said condition or disease may be selected from the group consisting of arthritis, migraine, and headache.

Said condition or disease may be associated with the gastrointestinal tract, wherein said condition or disease may be peptic ulcer, heartburn, reflux esophagitis, erosive esophagitis, non-ulcer dyspepsia, infection by *Helicobacter pylori*, alrynitis, and irritable bowel syndrome.

Said condition or disease may be selected from the group consisting of hyperalgesia and allodynia, or said condition or disease may be related to mucus secretion, wherein said mucus secretion is gastrointestinal, or occurs in the nose, sinuses, throat, or lungs.

Said condition or disease is related to abdominal cramping, e.g. said condition, menstrual cramping or disease may be irritable bowel syndrome.

Said condition or disease may be a bleeding disorder, or a sleep disorder, or mastocytosis.

Said condition or disease may be associated with elevated body temperature, or ocular hypertension and glaucoma, or ocular hypotension.

Said condition may relate to surgical procedures to treat pain, inflammation and other unwanted sequelae wherein said surgical procedure includes incision, laser surgery or implantation.

The present invention also relates to a method of treating inflammation resulting from inflammatory diseases characterized by monocytic infiltration caused by the secretion of cytokines and/or chemokines by administration, to a patient in need of said treatment, of a pharmaceutical composition comprising a compound of the present invention The current finding that the compounds of this invention are effective in attenuating the production of TNF family cytokines (TNFα), and the classical interleukin-1 (IL-1) family cytokines is especially important. These cytokines exert a broad spectrum of biological and pathological effects. They play key roles in inflammation and RA pathogenesis by stimulating the release of multiple proinflammatory cytokines, including themselves, through the NFκB signaling pathway. Although alleviating the symptoms of RA in 50-65% of patients, a TNFα antibody is very expensive to use compared to chemically synthesized small molecules, inconvenient to administer usually requiring injections, and has been linked to tuberculosis, lymphoma, and other adverse effects. Unlike a TNFα antibody that totally eliminates all circulating TNFα in the system; the compounds of this invention only attenuate the production of TNFα by inhibiting proinflammatory PG receptors. Therefore, the adverse effects associated with a TNFα antibody in elevating infectious and cancerous tendency is less likely.

Proinflammatory elements TNF, RANTES, and MCP-1 are involved in the cascade of events in the early and late stages of atherosclerosis. Plasma MCP-1 levels have been linked to cardiovascular disease risk factors in clinical studies. Platelet activation leads to the release of MIP-1α, RANTES, and IL-8, which attract leukocytes and further activate other platelets. These evidences provide a direct linkage between homeostasis, infection, and inflammation and the development of atherosclerosis. The compounds of this invention are able to target multiple biomarkers of inflammation, thrombosis, and atherothrombosis simultaneously, which may confer pharmaceutical potential on the compounds of this invention in treating atherosclerosis and atherothrombosis. As a result, the compounds of this invention are unlikely to be associated with cardiovascular liability as in the case of the COXIBs, conversely it may even have a beneficial effect on cardiovascular function.

In summary, because of their ability to suppress the synthesis of some key proinflammatory cytokines/chemokines IL-8, MCP-1, MDC, RANTES, and TNFα, the compounds of the present invention are believed to be, not only at least as effective as COXIBs and NSAIDs in RA treatment, but also are a safer therapy in RA treatment. They are also a potential therapy for cardiovascular diseases.

The compounds of this invention are believed to treat or prevent inflammation at least in part by the decreasing the amount of the secretion of certain cytokines and/or chemokines that result from the exposure of the patient to a stimulant.

In particular, the secretion of VEGF, MIP-1β, IL-8, MCP-1, MDC, and RANTES may be reduced in those instances where said secretions are triggered by lipopolysaccharides (LPS) and or TNFα.

Interleukin-8 (IL-8): functions as a potent chemoattractant and activator of neutrophils, IL-8 is produced in response to stimulation with either IL-1 or TNFα. IL-8 not only accounts for a significant proportion of the chemotactic activity for neutrophils in rheumatoid arthritis (RA) synovial fluids, but also is a potent angiogenic factor in the RA synovium.

Monocyte chemoattractant protein-1 (MCP-1, or CCL-2): is not only believed to play a role in inflammatory diseases characterized by monocytic infiltration, such as RA rheumatoid arthritis, psoriasis, and atherosclerosis, but is also implicated in other diseases, such as atopic dermatitis, renal disease, pleurisy, allergy and asthma, colitis, endometriosis, polymyositis and dermatomyositis, uveitis, restenosis, brain inflammation and obesity. MCP-1 also controls leukocyte trafficking in vascular cells involved in diabetes and diabetes-induced atherosclerosis. MCP-1 antibodies are potential therapeutic agents for treating MCP-1/CCR2-mediated multiple inflammatory diseases.

Tumor necrosis factor α (TNFα): mainly secreted by macrophages and recognized for its importance in activating the cytokine cascade. TNFα stimulates the production of proinflammatory cytokines/chemokines, collagenases, metalloproteinases, and other inflammatory mediators; activates endothelial cells and neutrophils; promotes T- and B-cell growth, as well as stimulating bone resorption. The TNFα antibody infliximab not only decreases the production of local and systemic proinflammatory cytokines/chemokines, but also reduces serum MMP-3 production, nitric oxide synthase activity, VEGF release, and angiogenesis in inflamed joints.

Macrophage-derived chemokine (MDC) induces chemotaxis for monocyte-derived dendritic cells, activated T cells and natural killer (NK) cells (Ho et al., 2003). Highly expressed by the three major cell types involved in allergic inflammation: eosinophils, basophils, and Th2 lymphocytes (Garcia et al., 2005), as well as highly expressed in atopic dermatitis (Pivarcsi et al., 2005), MDC plays a role in inflammatory diseases such as allergic asthma and atopic dermatitis (Ho et al., 2003). Significantly enhanced in keratinocytes of patients with atopic dermatitis, MDC could be a candidate therapeutic target for inflammatory skin disease such as atopic dermatitis (Qi et al., 2009). MDC is also implicated in disease activity of RA. After combination treatment with the disease-modifying anti-rheumatic drugs leflunomide and methotrexate in RA patients, plasma MCP-1 and MDC concentrations were significantly lower, and so was the recruitment of inflammatory cells into the sites of inflammation (Ho et al., 2003). Moreover, MDC also amplify platelet activation and has been associated with the pathogenesis of atherosclerotic disease including thrombosis (Gleissner et al., 2008).

Regulated on Activation, Normal T Cell Expressed and Secreted (RANTES) is a chemoattractant for blood monocytes, memory T-helper cells and eosinophils, and plays an active role in recruiting leukocytes into inflammatory sites. It also stimulates the release of histamine from basophils, activates eosinophils and causes hypodense eosinophils, which are associated with diseases such as asthma and allergic rhinitis. RANTES receptor CCR5 is also expressed on cells involved in atherosclerosis (e.g. monocytes/macrophages, T lymphocytes, or Th1-type cells), and is specialized in mediating RANTES-triggered atherosclerotic plaque formation (Zernecke et al., 2008). Like MCP-1, stimulation with RANTES enhances production of IL-6 and IL-8 in RA fibroblast-like synovial cells; elevated MMP-3 production by chondrocytes, and inhibited proteoglycan synthesis and enhanced proteoglycan release from the chondrocytes (Iwamoto et al., 2008). Both MCP-1 and RANTES were found to play an important role in allergic lung inflammation, lung leukocyte infiltration, bronchial hyper-responsiveness, and the recruitment of eosinophils in the pathogenesis of asthma (Conti et al., 2001). Similar to MCP-1, RANTES also enhances the inflammatory response within the nervous system, which plays an apparent role in the pathogenesis of multiple sclerosis (Conti et al., 2001). Inhibitors for RANTES may provide clinical benefits in treating inflammation, CNS disorders, parasitic disease, cancer, autoimmune and heart diseases (Castellani et al., 2007).

While the use of the compounds of this invention are believed to decrease the secretion of the above cytokines, it is also believed that the compounds of this invention are effective to decrease the secretion of ENA-7, PAI-1, CD-10, G-CSF, GM-CSF, IL-1α and IL-18, as well.

The compounds of this invention may be also tested for efficacy in treating uveitis as described below.

Arachidonate Induced Uveitis

The rational for this protocol is to use arachidonate to directly produce ocular anterior segment uveitis, as opposed to using lipopolysaccharide (LPS) to indirectly release arachidonic acid.

Induction of Uveitis:

Conscious male or female Dutch-belted pigmented rabbits weighing 2.5-3 kg are used for all in vivo slit lamp studies. Four animals are employed per test group. The right eye of each animal receiving 35 µl of topically administered test and the contralateral left eye of each animal receiving 35 µl of topically administered vehicle (t=0 minutes), followed 30 minutes later by treatment with 35 µl of 0.5% sodium arachidonate onto the surface of both eyes (t=30 minutes). Both eyes are examined by slit lamp 60 minutes following sodium arachdionate challenge (t=90 minutes) at 16× magnification under both white light and blue light illumination at an approximate angle of 45° through 1 mm and 5 mm slit widths.

Measurement of Anterior Chamber Leukocyte Infiltration:

Anterior chamber leukocyte infiltration is measured using a numerical scoring system to estimate cell number per field defined by a 5 mm slit width: 0=no cells per field (no response); 1=1–10 cells per field (mild); 2=11–20 cells per field (moderate); 3=26–50 cells per field (severe); 4=>50 cells per filed (florid). Results are reported as the mean score value±S.E.M.

The compounds of this invention may be tested according to the method described in "Characterization of Receptor Subtypes Involved in Prostanoid-Induced Conjunctival Pruritis and Their Role in Mediating Conjunctival Itching", Vol. 279, No. 1, (JPET) 279, 137-142' 1996 for their efficacy in alleviating itch to thereby indicate that the compounds of this invention are useful in treating allergic conjunctivitis.

While the use of the compounds of this invention are believed to decrease the secretion of the above cytokines, it also is believed that the compounds of this invention are effective to decrease the secretion of ENA-7, PAI-1, CD-10, G-CSF, GM-CSF, IL-1α and IL-18, as well.

Finally, said condition that may be treated with the compounds of this invention may be related to pain and inflammation and post-surgical scar and keloid formation.

In view of the various diseases and conditions that may be treated with the compositions of this invention there is provided a pharmaceutical product comprising a compound having the following formula

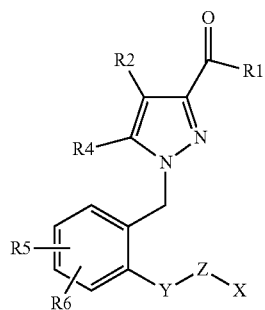

wherein Y is $(CH_2)_m$ wherein m is 0 or an integer of from 1 to 3;
Z is selected from the group consisting of O, S, SO, $SO_2$ and $(CH_2)_p$, wherein p is 0 or an integer of from 1 to 3;
W is substituted aryl, alkyl, substituted alkyl, cycloalkyl or substituted cycloalkyl:
$R_1$ is selected from the group consisting of $OR_7$, $N(R_7)_2$, and $N(R_7)SO_2R_7$;
$R_2$ is H;
$R_4$ is selected from the group consisting of alky, halogen-substituted alkyl and amino,
$R_5$ is selected from the group consisting of H, hydroxyl, alkyl, aryl, alkoxy, aryloxy, halogen, nitro, amino, cyano and hydroxyl, halogen, nitro, amino and cyano-substituted alkyl, aryl, alkoxy or aryloxy;
$R_6$ is selected from the group consisting of H, hydroxyl, alkyl, aryl, alkoxy, aryloxy, halogen, nitro, amino, cyano and hydroxyl, halogen, nitro, amino and cyano-substituted alkyl, aryl, alkoxy or aryloxy, wherein at least one of $R_5$ and $R_6$ is halogen; and
$R_7$ is selected from the group consisting of H, hydrocarbyl and substituted hydrocarbyl and/or a pharmaceutically acceptable salt or a prodrug thereof, wherein said product is packaged and labeled for the treatment or prevention of a disease or condition selected from the group consisting of uveitis, allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, hyperpyrexia, endometriosis gangrene, glaucoma, hypothermia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, pain, perennial rhinitis, pre-term labor pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, sports injuries, muscle aches and pains, and surgical adjunct for minimizing pain, inflammation and scar/keloid formation.

Those skilled in the art will readily understand that for administration the compounds disclosed herein can be admixed with pharmaceutically acceptable excipients which, per se, are well known in the art. Specifically, a drug to be administered systemically, it may be formulated as a powder, pill, tablet or the like, or as a solution, emulsion, suspension, aerosol, syrup or elixir suitable for oral or parenteral administration or inhalation.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the compounds of the present invention and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectable formulations can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds of the present invention administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 ng/kg/day or about 1 ng/kg/day to about 100 mg/kg/day.

For ophthalmic application, solutions are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

Similarly, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

For topical use, creams, ointments, gels, solutions or suspensions, etc., containing the compound of the present invention are employed. Topical formulations may generally be comprised of a pharmaceutical carrier, cosolvent, emulsifier, penetration enhancer, preservative system, and emollient.

The actual dose of the compounds of the present invention depends on the specific compound, and on the condition to be treated; the selection of the appropriate dose is well within the knowledge of the skilled artisan.

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. It is intended that all such modifications will fall within the scope of the appended claims.

We claim:
1. A compound represented by the following formula

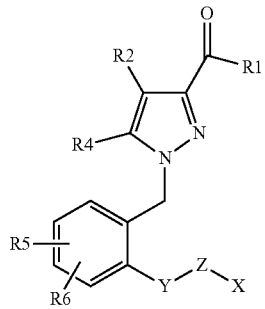

or a pharmaceutically acceptable salt or a prodrug thereof, wherein:
Y is $(CH_2)_m$ wherein m is 0 or an integer of from 1 to 3;
Z is selected from the group consisting of O, S, SO, $SO_2$ and $(CH_2)_p$, wherein p is 0 or an integer of from 1 to 3;
W is substituted aryl, alkyl, substituted alkyl, cycloalkyl or substituted cycloalkyl:
$R_1$ is selected from the group consisting of $OR_7$, $N(R_7)_2$, and $N(R_7)SO_2R_7$;
$R_2$ is H;
$R_4$ is selected from the group consisting of alkyl, halogen-substituted alkyl and amino
$R_5$ is selected from the group consisting of H, hydroxyl, alkyl, aryl, alkoxy, aryloxy, halogen, nitro, amino, cyano and hydroxyl, halogen, nitro, amino and cyano-substituted alkyl, aryl, alkoxy or aryloxy;
$R_6$ is selected from the group consisting of H, hydroxyl, alkyl, aryl, alkoxy, aryloxy, halogen, nitro, amino, cyano and hydroxy, halogen, nitro, amino and cyano-substituted alkyl, aryl, alkoxy or aryloxy, wherein at least one of $R_5$ and $R_6$ is halogen; and
$R_7$ is selected from the group consisting of H, hydrocarbyl and substituted hydrocarbyl.

2. The compound according to claim 1, wherein the compound is selected from the group consisting of:
1-(2-Cyclopentylmethoxy-5-trifluoromethyl-benzyl)-5-methyl-1H-pyrazole-3-carboxylic acid;
N-{1-[5-Chloro-2-(4-methoxy-benzyloxy)-benzyl]-5-methyl-1H-pyrazole-3-carbonyl}-benzenesulfonamide;
N-{1-[5-Chloro-2-(4-Chloro-benzyloxy)-benzyl]-5-methyl-1H-pyrazole-3-carbonyl}-benzenesulfonamide;
1-[5-Bromo-2-(2-ethyl-butoxy)-benzyl]-5-methyl-1H-pyrazole-3-carboxylic acid;
1-[5-Bromo-2-(2-ethyl-2-methyl-butoxy)-benzyl]-5-methyl-1H-pyrazole-3-carboxylic acid; and
1-[5-Bromo-2-(1-trifluoromethyl-cyclobutylmethoxy)-benzyl]-5-methyl-1H-pyrazole-3-carboxylic acid;
and pharmaceutically acceptable salts thereof.

3. A pharmaceutical composition comprising a compound according to claim 1, or a pharmaceutically acceptable salt or a prodrug thereof, or a pharmaceutically acceptable salt or a prodrug thereof.

4. A pharmaceutical composition comprising a compound according to claim 2, or a pharmaceutically acceptable salt or a prodrug thereof, or a pharmaceutically acceptable salt or a prodrug thereof.

* * * * *

UNITED STATES PATENT AND TRADEMARK OFFICE
CERTIFICATE OF CORRECTION

| | |
|---|---|
| PATENT NO. | : 9,522,890 B2 |
| APPLICATION NO. | : 14/798143 |
| DATED | : December 20, 2016 |
| INVENTOR(S) | : William R. Carling et al. |

It is certified that error appears in the above-identified patent and that said Letters Patent is hereby corrected as shown below:

On the Title Page

In item (72), in Column 1, in "Inventors", Line 2, delete "Baslidon" and insert -- Basildon --, therefor.

In item (72), in Column 1, in "Inventors", Line 3, delete "Safran Walden" and insert -- Saffron Walden --, therefor.

In the Specification

In Column 1, Line 10, delete "No." and insert -- No.: --, therefor.

In Column 2, Line 42, after "thereof" insert -- . --.

In Column 2, Line 48, after "cyclopentyl" insert -- . --.

In Column 3, Line 50, after "alkyl" insert -- . --.

In Column 3, Line 61, after "cyclopentyl" insert -- . --.

In Column 4, Line 2, after "acid" insert -- . --.

In Column 4, Line 45, after "alkyl" insert -- . --.

In Column 4, Line 52, after "O." delete "is 0.".

In Column 4, Line 54, after "cyclopentyl" insert -- . --.

In Column 4, Line 62, after "acid" insert -- . --.

Signed and Sealed this
Twenty-eighth Day of February, 2017

Michelle K. Lee
*Director of the United States Patent and Trademark Office*

CERTIFICATE OF CORRECTION (continued)
U.S. Pat. No. 9,522,890 B2

In Column 5, Line 13, delete "metastic" and insert -- metastatic --, therefor.

In Column 5, Line 26, delete "ophthalmogical" and insert -- ophthalmological --, therefor.

In Column 5, Line 57, delete "alrynitis," and insert -- laryngitis, --, therefor.

In Column 6, Line 27, after "labor" insert -- . --.

In Column 6, Line 28, delete "57" and insert -- 57. --, therefor.

In Column 6, Line 65, delete "hydrocarbyl." and insert -- hydrocarbyl, --, therefor.

In Columns 6-7, Lines 66-67 and 1-23, delete "or a pharmaceutically acceptable salt or a prodrug thereof, wherein said product is packaged and labeled for the treatment or prevention of a disease or condition selected from the group consisting of uveitis, allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, endometriosis fertility disorders, hyperpyrexia, gangrene, glaucoma, hypothermia, immune and autoimmune diseases, inflammatory conditions, menstrual cramping, metastatic tumor growth, migraine, mucus secretion disorders, nasal congestion, nasal inflammation, occlusive vascular diseases, ocular hypertension, ocular hypotension, osteoporosis, pain, perennial rhinitis, pre-term labor pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, sports injuries, muscle aches and pains, and surgical adjunct for minimizing pain, inflammation and scar/keloid formation." and insert the same on Column 6, Line 65 as the continuation of the same Paragraph.

In Column 7, Line 13, delete "metastic" and insert -- metastatic --, therefor.

In Column 9, Line 27, delete "of" and insert -- of: --, therefor.

In Column 10, Line 31, delete "ArH,)," and insert -- ArH), --, therefor.

In Column 10, Line 36, delete "1 h" and insert -- 1h --, therefor.

In Column 10, Line 60, delete "dessicator" and insert -- desiccator --, therefor.

In Column 11, Line 4, delete "1 h" and insert -- 1h --, therefor.

In Column 11, Line 36, delete "(m. 1H" and insert -- (m, 1H, --, therefor.

CERTIFICATE OF CORRECTION (continued)
U.S. Pat. No. 9,522,890 B2

In Column 11, Line 43, delete "1 h" and insert -- 1h --, therefor.

In Column 11, Line 67, delete "dessicator" and insert -- desiccator --, therefor.

In Column 12, Line 5, delete "(m. 1H" and insert -- (m, 1H, --, therefor.

In Column 12, Lines 46-47, delete "bromosalicaldehyde" and insert -- bromosalicylaldehyde --, therefor.

In Column 12, Line 49, delete "ArH,)," and insert -- ArH), --, therefor.

In Column 12, Line 54, delete "1 h" and insert -- 1h --, therefor.

In Column 13, Line 13, delete "1 h" and insert -- 1h --, therefor.

In Column 13, Line 36, delete "$OCH_2CH$,)" and insert -- $OCH_2CH$), --, therefor.

In Column 13, Line 36, delete "$CH_2$)," and insert -- $CH_3$), --, therefor.

In Column 13, Line 37, delete "$CH_2CH_2$)." and insert -- $CH_2CH_3$). --, therefor.

In Column 13, Line 43, delete "1 h" and insert -- 1h --, therefor.

In Column 13, Line 64, delete "(dd 1H," and insert -- (dd, 1H, --, therefor.

In Column 13, Line 65, delete "(m. 1H" and insert -- (m, 1H, --, therefor.

In Column 13, Line 66, delete "CHd," and insert -- $CH_3$), --, therefor.

In Column 14, Lines 41-42, delete "trifluoromethylalisaldehyde" and insert -- trifluoromethylsalicylaldehyde --, therefor.

In Column 14, Lines 51-52, delete "1 h" and insert -- 1h --, therefor.

In Column 15, Line 11, delete "1 h" and insert -- 1h --, therefor.

In Column 15, Line 36, delete "$CH_2$)," and insert -- $CH_3$), --, therefor.

In Column 15, Line 43, delete "1 h" and insert -- 1h --, therefor.

In Column 15, Line 64, delete "(d 1H," and insert -- (d, 1H, --, therefor.

In Column 15, Line 65, delete "(m. 1H" and insert -- (m, 1H, --, therefor.

In Column 15, Line 66, delete "CHO." and insert -- $CH_3$), --, therefor.

CERTIFICATE OF CORRECTION (continued)

In Column 16, Line 31, delete "1 h" and insert -- 1h --, therefor.

In Column 16, Line 63, delete "ArH,)," and insert -- ArH), --, therefor.

In Column 17, Line 4, delete "1 h" and insert -- 1h --, therefor.

In Column 17, Line 36, delete "ArH,)," and insert -- ArH), --, therefor.

In Column 17, Line 44, delete "1 h" and insert -- 1h --, therefor.

In Column 18, Line 7, delete "ArH,)," and insert -- ArH), --, therefor.

In Column 18, Line 17, delete "1 h" and insert -- 1h --, therefor.

In Column 18, Line 62, delete "ArH,)," and insert -- ArH), --, therefor.

In Column 18, Line 63, delete "ArH,)," and insert -- ArH), --, therefor.

In Column 18, Line 63, delete "ArH,)," and insert -- ArH), --, therefor.

In Column 18, Line 66, delete "$OCH_2$)," and insert -- $OCH_3$), --, therefor.

In Column 19, Line 38, delete "ArH,)," and insert -- ArH), --, therefor.

In Column 20, Line 4, delete "2-(-2" and insert -- 2-(2 --, therefor.

In Column 20, Lines 4-5, delete "1 h" and insert -- 1h --, therefor.

In Column 20, Line 29, delete "$CH_2$)," and insert -- $CH_3$), --, therefor.

In Column 20, Line 31, delete "$CH_2CH_2$)." and insert -- $CH_2CH_3$). --, therefor.

In Column 20, Lines 40-41, delete "1 h" and insert -- 1h --, therefor.

In Column 20, Line 63, delete "CHO," and insert -- $CH_3$), --, therefor.

In Column 21, Line 54, delete "$CH_3CH_3$)." and insert -- $CH_2CH_3$). --, therefor.

In Column 22, Line 23, delete "1 h" and insert -- 1h --, therefor.

In Column 22, Line 53, delete "ditert-" and insert -- di-tert- --, therefor.

In Column 23, Line 5, delete "1 h" and insert -- 1h --, therefor.

In Column 24, Line 4, delete "1 h" and insert -- 1h --, therefor.

CERTIFICATE OF CORRECTION (continued)
U.S. Pat. No. 9,522,890 B2

In Column 24, Line 24, delete "ditert-" and insert -- di-tert- --, therefor.

In Column 24, Line 36, delete "CH$_2$)," and insert -- CH$_3$), --, therefor.

In Column 24, Line 42, delete "1 h" and insert -- 1h --, therefor.

In Column 24, Line 59, delete "-(5-" and insert -- 1-(5- --, therefor.

In Column 24, Line 60, delete "1 h" and insert -- 1h --, therefor.

In Column 25, Line 2, delete "1 h" and insert -- 1 h --, therefor.

In Column 25, Lines 3-6, delete "$^1$H-NMR (CDCl$_3$, 300 MHz) δ 7.32 (d, 1H, ArH), 6.70 (m, 2H, ArH), 6.67 (s, 1H, ArH), 5.32 (s, 2H, ArCH$_2$), 3.97 (d, 2H, OCH$_2$), 2.75 (m, 1H, CH), 2.20 (s, 3H, CH$_3$), 2.10-1.80 (m, 6H, CCH$_2$)" and insert the same on Column 25, Line 4 as a new Paragraph.

In Column 25, Line 6, after ")" insert -- . --.

In Column 25, Line 35, after ")" insert -- . --.

In Column 25, Line 47, delete "haemagglutanin" and insert -- hemagglutinin --, therefor.

In Column 25, Line 66, delete "Signaling" and insert -- signaling --, therefor.

In Column 27, Line 54, delete "metastic" and insert -- metastatic --, therefor.

In Column 27, Line 66, delete "ophthalmogical" and insert -- ophthalmological --, therefor.

In Column 28, Line 18, delete "alrynitis," and insert -- laryngitis, --, therefor.

In Column 28, Line 41, after "invention" insert -- . --.

In Column 29, Line 26, delete "and or" and insert -- and/or --, therefor.

In Column 29, Line 37, delete "arthritus," and insert -- arthritis, --, therefor.

In Column 30, Line 61, delete "arachdionate" and insert -- arachidonate --, therefor.

In Column 31, Lines 8-9, delete "Pruritis" and insert -- Pruritus --, therefor.

In Column 31, Line 10, delete "(JPET) 279," and insert -- (JPET)279, --, therefor.

In Column 31, Line 49, delete "alky," and insert -- alkyl, --, therefor.

CERTIFICATE OF CORRECTION (continued)
U.S. Pat. No. 9,522,890 B2

In Column 32, Line 7, delete "metastic" and insert -- metastatic --, therefor.

In Column 32, Line 36, delete "distcarate" and insert -- distearate --, therefor.

In the Claims

In Column 34, Line 30, in Claim 1, after "amino" insert -- ; --.